(12) United States Patent
Reiner et al.

(10) Patent No.: US 10,512,700 B2
(45) Date of Patent: Dec. 24, 2019

(54) RADIOHALIDE-LABELED TARGETED DIAGNOSTICS AND THERAPEUTICS

(71) Applicant: Memorial Sloan Kettering Cancer Center, New York, NY (US)

(72) Inventors: Thomas Reiner, Weehawken, NJ (US); Jason S. Lewis, New York, NY (US); Wolfgang Weber, Larchmont, NY (US); Beatriz Salinas Rodriguez, Madrid (ES); Brandon Carney, Brooklyn, NY (US); Giuseppe Carlucci, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/506,001

(22) PCT Filed: Aug. 27, 2015

(86) PCT No.: PCT/US2015/047127
§ 371 (c)(1),
(2) Date: Feb. 23, 2017

(87) PCT Pub. No.: WO2016/033293
PCT Pub. Date: Mar. 3, 2016

(65) Prior Publication Data
US 2017/0266327 A1    Sep. 21, 2017

Related U.S. Application Data

(60) Provisional application No. 62/042,540, filed on Aug. 27, 2014.

(51) Int. Cl.
| | |
|---|---|
| *A61K 51/04* | (2006.01) |
| *A61K 45/06* | (2006.01) |
| *C07D 237/32* | (2006.01) |
| *C07D 403/14* | (2006.01) |
| *C07F 5/02* | (2006.01) |

(52) U.S. Cl.
CPC .......... *A61K 51/0459* (2013.01); *A61K 45/06* (2013.01); *C07D 237/32* (2013.01); *C07D 403/14* (2013.01); *C07F 5/022* (2013.01)

(58) Field of Classification Search
CPC combination set(s) only.
See application file for complete search history.

(56) References Cited

U.S. PATENT DOCUMENTS

2012/0010204 A1    1/2012  Martin et al.
2013/0309170 A1    11/2013 Reiner et al.

OTHER PUBLICATIONS

Reiner et al., Neoplasia (2012) 14, 169-177 (Year: 2012).*
Zhou et al., "Synthesis, [a8F] radiolabeling, and evaluation of poly (ADP-ribose) polymerase-1 (PARP-1) inhibitors for in vivo imaging of PARP-1 using positron emission tomography," Bioorg. Med. Chem., vol. 22, No. 5, pp. 1700-1707 (Mar. 2014).
Keliher et al., "Efficient acid-catalyzed 18F/19F fluoride exchange of BODIPY Dyes," Chem. Med. Chem., vol. 9, No. 7, pp. 1368-1373 (Jul. 2014).
International Search Report and Written Opinion, PCT/US2015/047127, Memorial Sloan Kettering Cancer Center (dated Dec. 14, 2015).

* cited by examiner

*Primary Examiner* — Robert S Cabral
(74) *Attorney, Agent, or Firm* — Foley & Lardner LLP

(57) ABSTRACT

Disclosed are chemical entities of formula (I) wherein $R_1$, $R_2$ and n are defined herein, and methods of use thereof. These chemical entities are radiative emitters and are useful, e.g., as therapeutic agents for the treatment of, or as diagnostic (e.g., imaging) agents for cancers, e.g., cancers in which PARP1 is overexpressed.

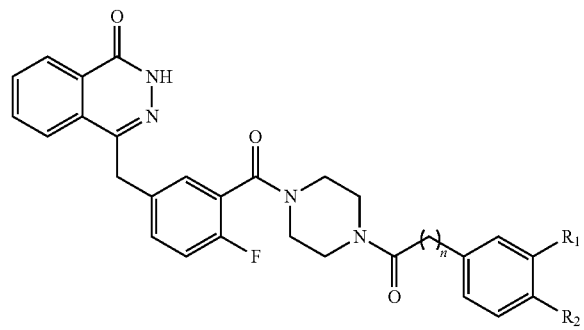

(I)

52 Claims, 5 Drawing Sheets

RADIOHALIDE-LABELED TARGETED DIAGNOSTICS AND THERAPEUTICS

This application is a national stage entry of International Patent Application No. PCT/US2015/047127 filed on Aug. 27, 2015, which claims priority to U.S. Provisional Patent Application No. 62/042,540 filed on Aug. 27, 2014, the entire contents of each of which are hereby incorporated by reference.

BACKGROUND

The National Cancer Institute estimates that 23,380 adults (12,820 men and 10,560 women) will be diagnosed with brain and other nervous system tumors in 2014 in the United States alone. Glioblastoma is a particularly aggressive and invasive form of brain cancer, and the median survival ranges from 31.9 months for patients 20-29 years of age to only 5.6 months in patients 80 years and older. (D. R. Johnson and B. P. O'Neill, "Glioblastoma survival in the United States before and during the temozolomide era", *J. Neurooncol.* 2012, 107:359-64). One method for improving median survival in glioblastoma patients is to increase the completeness of tumor tissue resected during surgery, while not increasing the amount of healthy brain tissue removed. (W. Stummer et al., "Extent of resection and survival in glioblastoma multiforme: identification of and adjustment for bias", *Neurosurgery* 2008, 62:564-76; B. Chen et al., "Gross total resection of glioma with the intraoperative fluorescence-guidance of fluorescein sodium", *Int. J. Med. Sci.* 2012, 9:708-14). In clinical practice however, the distinction between malignant growth and healthy brain tissue can be difficult to make, and the resection of healthy brain increases the incidence of post-surgical morbidity.

Targeted radiation therapy is seen as an efficient technique of selectively ablating malignant growth while sparing surrounding tissues. These efforts, however, are often stricken by failure to deliver sufficiently high concentrations of therapeutic nuclides to cancer cells while keeping the radiation dose to excretory organs and bone marrow within safe limits.

SUMMARY

The present invention, among other things, addresses the need for appropriate vectors to deliver radioisotopes to tumor tissues while limiting deleterious effects, for example, due to off-target toxicities.

In some embodiments, the present invention encompasses the insights (1) that chemical entities of formula (I)

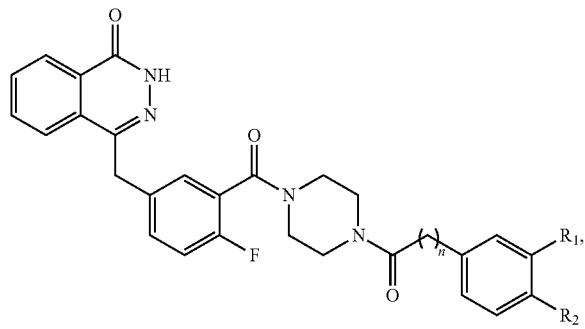

wherein $R_1$, $R_2$ and n are defined herein, possess biophysical properties suitable to sufficiently selectively accumulate in nuclei of certain malignant cells; and (2) that a provided chemical entity of formula (i) containing a radiohalide such that the chemical entity is a radiative emitter (e.g., auger electron emitter, alpha emitter, beta emitter) and can serve as a therapeutic agent, e.g., by delivering radiation to a malignant cell, or a diagnostic agent, e.g., by emitting detectable radiation in the vicinity of a malignant cell.

DETAILED DESCRIPTION OF CERTAIN EMBODIMENTS

Chemical Entities

Figure 1A:
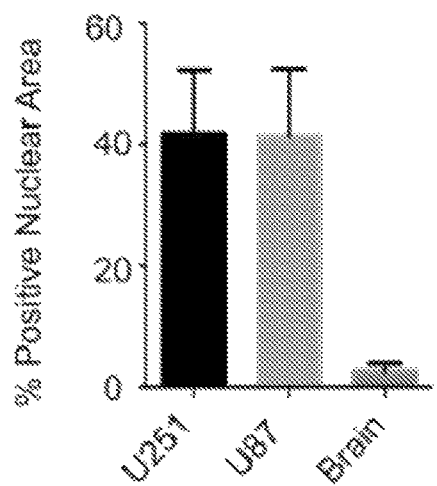
FIG. 1A illustrates the percent of nuclei positive for PARP1 in different tissue types.

In some aspects, the invention provides chemical entities that are radiative emitters. In some embodiments, a provided radiative emitter is a chemical entity of formula (I):

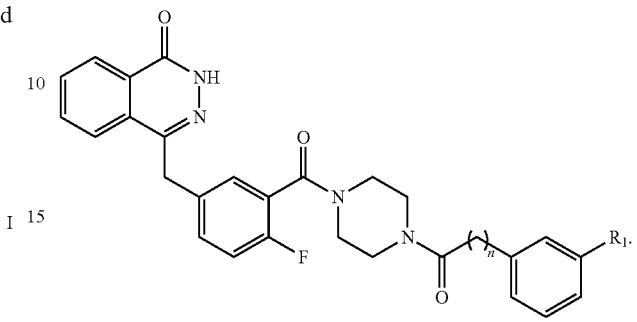

I wherein one of $R_1$ and $R_2$ is $^{123}I$, $^{124}I$, $^{125}I$, $^{131}I$, $^{211}At$, or $^{18}F$, and the other is $^{123}I$, $^{124}I$, $^{125}I$, $^{131}I$, $^{211}At$, $^{18}F$ or H; and n is 0, 1 or 2.

Unless otherwise specified or clear from context, the term "chemical entity" refers to a compound having the indicated structure, whether in its "free" form (e.g., "free compound" or "free base" or "free acid" form, as applicable), or in a salt form, particularly a pharmaceutically acceptable salt form, and furthermore whether in solid state form or otherwise. In some embodiments, a solid state form is an amorphous (i.e., non-crystalline) form; in some embodiments, a solid state form is a crystalline form (e.g., a polymorph, pseudohydrate, or solvate such as a hydrate). Similarly, the term encompasses the compound whether provided in solid form or otherwise. Unless otherwise specified, all statements made herein regarding "compounds" apply both to the free compounds and to chemical entities of the compounds.

As is customary in the art, when an atom in a chemical structure is identified as being a particular isotope, the intended meaning is that the isotope is present in a greater (percentage) amount than its natural abundance. The natural abundance of stable isotopes has been reported, e.g., in the 1997 report of the IUPAC Subcommittee for Isotopic Abundance Measurements by K. J. R. Rosman and P. D. P. Taylor, *Pure Appl. Chem.* 1999; 71:1593-1607. The natural abundance of each of $^{123}I$, $^{124}I$, $^{125}I$, $^{131}I$, $^{211}At$ and $^{18}F$ is considered to be 0%.

In some embodiments, a provided radiative emitter is a chemical entity of formula (I) wherein one of $R_1$ and $R_2$ is $^{123}I$, $^{124}I$, $^{125}I$, $^{131}I$, $^{211}At$ or $^{18}F$, and the other is H.

In some such embodiments, $R_1$ is $^{123}I$, $^{124}I$, $^{125}I$, $^{131}I$, $^{211}At$ or $^{18}F$, and $R_2$ is H, i.e., a chemical entity of formula (Ia):

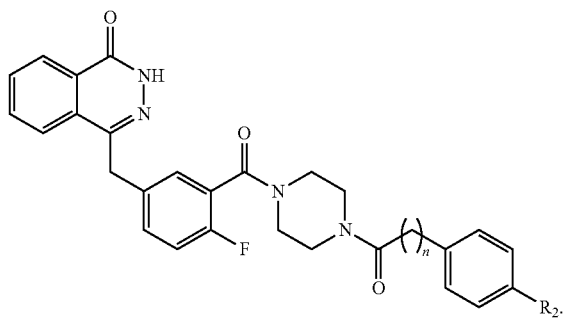

Ia

In some embodiments, $R_1$ is $^{123}I$, $^{124}I$, $^{125}I$, $^{131}I$ or $^{211}At$, and $R_2$ is H.

In some such embodiments, $R_1$ is H, and $R_2$ is $^{123}I$, $^{124}I$, $^{125}I$, $^{131}I$, $^{211}At$ or $^{18}F$, i.e., a chemical entity of formula (Ib):

Ib

In some embodiments, $R_1$ is H, and $R_2$ is $^{123}I$, $^{124}I$, $^{125}I$, $^{131}I$ or $^{211}At$.

In some embodiments, a provided radiative emitter is a chemical entity of formula (I) wherein one of $R_1$ and $R_2$ is $^{123}I$ or $^{125}I$, and the other is $^{123}I$, $^{125}I$ or H. Such a chemical entity is useful, e.g., as an Auger Electron emitter. When it contains $^{123}I$, such a chemical entity is useful, e.g., in single-photon emission computed tomography (SPECT). In some such embodiments, one of $R_1$ and $R_2$ is $^{123}I$ or $^{125}I$, and the other is H. In some such embodiments, one of $R_1$ and $R_2$ is $^{123}I$ and the other is H. In some such embodiments, one of $R_1$ and $R_2$ is $^{125}I$, and the other is H.

In some embodiments, a provided radiative emitter is a chemical entity of formula (Ia), wherein $R_1$ is $^{123}I$ or $^{125}I$. In some such embodiments, $R_1$ is $^{123}I$. In some such embodiments, $R_1$ is $^{125}I$.

In some embodiments, a provided radiative emitter is a chemical entity of formula (Ib) wherein $R_2$ is $^{123}I$ or $^{125}I$. In some such embodiments, $R_2$ is $^{123}I$. In some such embodiments, $R_2$ is $^{125}I$.

In some embodiments, a provided radiative emitter is a chemical entity of formula (I) wherein one of $R_1$ and $R_2$ is $^{131}I$ and the other is $^{131}I$ or H. Such a chemical entity is useful, e.g., as a beta emitter. Such a chemical entity is also useful, e.g., in SPECT imaging. In some such embodiments, one of $R_1$ and $R_2$ is $^{131}I$, and the other is H.

In some embodiments, a provided radiative emitter is a chemical entity of formula (Ia), wherein $R_1$ is $^{131}$I. In some embodiments, a provided radiative emitter is a chemical entity of formula (Ib) wherein $R_2$ is $^{131}$I.

In some embodiments, a provided radiative emitter is a chemical entity of formula (I) wherein one of $R_1$ and $R_2$ is $^{211}$At and the other is $^{211}$At or H. Such a chemical entity is useful, e.g., as an alpha emitter. In some such embodiments, one of $R_1$ and $R_2$ is $^{211}$At, and the other is H.

In some embodiments, a provided radiative emitter is a chemical entity of formula (Ia), wherein $R_1$ is $^{211}$At. In some embodiments, a provided radiative emitter is a chemical entity of formula (Ib) wherein $R_2$ is $^{211}$At.

In some embodiments, a provided radiative emitter is a chemical entity of formula (I) wherein one of $R_1$ and $R_2$ is $^{124}$I and the other is $^{124}$I or H. Such a chemical entity is useful, e.g., in positron emission tomography (PET). In some such embodiments, one of $R_1$ and $R_2$ is $^{124}$I, and the other is H.

In some embodiments, a provided radiative emitter is a chemical entity of formula (Ia), wherein $R_1$ is $^{124}$I. In some embodiments, a provided radiative emitter is a chemical entity of formula (Ib) wherein $R_2$ is $^{124}$I.

In some embodiments, a provided radiative emitter is a chemical entity of formula (I) wherein one of $R_1$ and $R_2$ is $^{18}$F and the other is $^{18}$F or H. Such a chemical entity is useful, e.g., in positron emission tomography (PET). In some such embodiments, one of $R_1$ and $R_2$ is $^{18}$F, and the other is H.

In some embodiments, a provided radiative emitter is a chemical entity of formula (Ia), wherein $R_1$ is $^{18}$F. In some embodiments, a provided radiative emitter is a chemical entity of formula (Ib) wherein $R_2$ is $^{18}$F.

In some embodiments, a provided radiative emitter is a chemical entity of formula (I) wherein n is 0. In some embodiments, a provided radiative emitter is a chemical entity of formula (Ia) wherein n is 0. In some embodiments, a provided radiative emitter is a chemical entity of formula (Ib) wherein n is 0. In some embodiments, a provided radiative emitter is a chemical entity of formula (I) wherein n is 1. In some embodiments, a provided radiative emitter is a chemical entity of formula (Ia) wherein n is 1. In some embodiments, a provided radiative emitter is a chemical entity of formula (Ib) wherein n is 1. In some embodiments, a provided radiative emitter is a chemical entity of formula (I) wherein n is 2. In some embodiments, a provided radiative emitter is a chemical entity of formula (Ia) wherein n is 2. In some embodiments, a provided radiative emitter is a chemical entity of formula (Ib) wherein n is 2.

Exemplary radiative emitters of formula (I) are shown in Table 1, below, in which I* is $^{123}$I (C-1a to C-6a), I* is $^{124}$I (C-1b to C-6b), I* is $^{125}$I (C-1c to C-6c), or I* is $^{131}$I (C-1d to C-6d). Additional exemplary radiative emitters of formula (I) are analogous compounds in which 1* is replaced with $^{211}$At (C-1e to C-6e) or $^{18}$F (C-1f to C-6f). Throughout this application, radiative emitters are sometimes written with the radionuclide expressly identified, e.g., "C-2b ($^{124}$I)". However, this express identification is gratuitous, as "C-2b" unambiguously identifies the compound C-2, below, in which I* represents $^{124}$I. Accordingly, the terms are used interchangeably, and no inference should be drawn from the presence or absence of the express identification of radionuclide.

TABLE 1

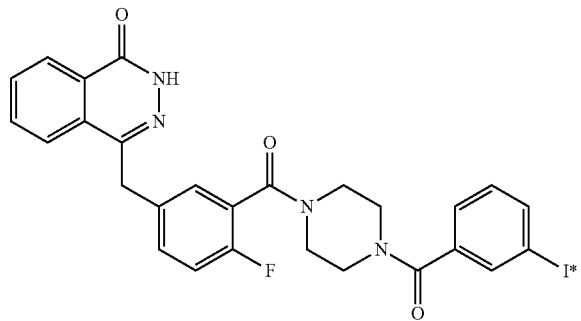

C-1

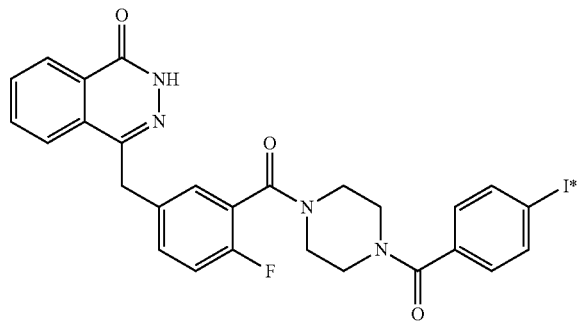

C-2

TABLE 1-continued
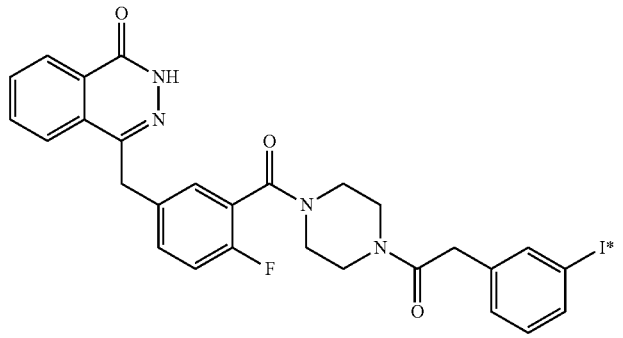
C-3
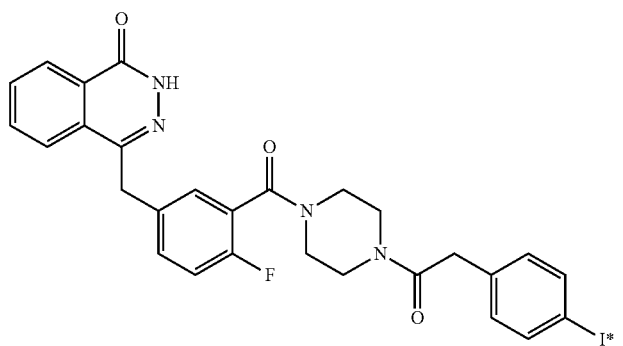
C-4
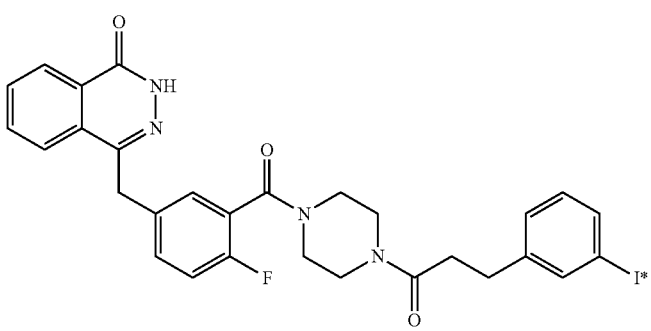
C-5
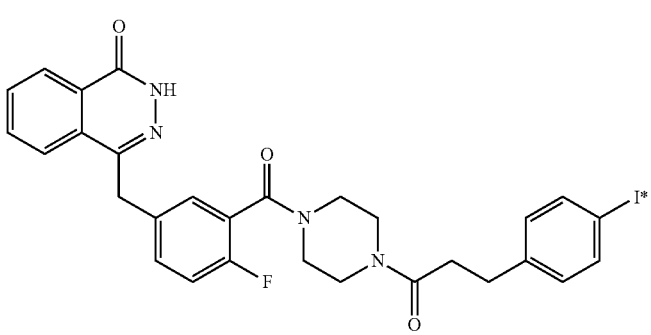
C-6

In some embodiments, a provided radiative emitter is the chemical entity C-2a, that is, the compound:

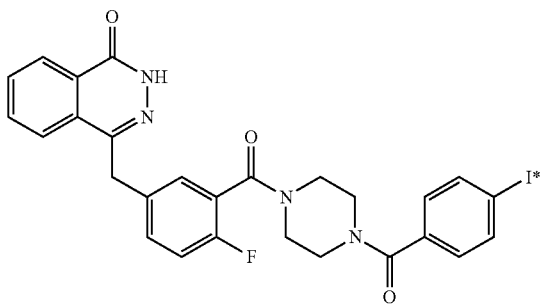

wherein I* is $^{123}$I, or a pharmaceutically acceptable salt thereof.

In some embodiments, a provided radiative emitter is the chemical entity C-2b, that is, the compound:

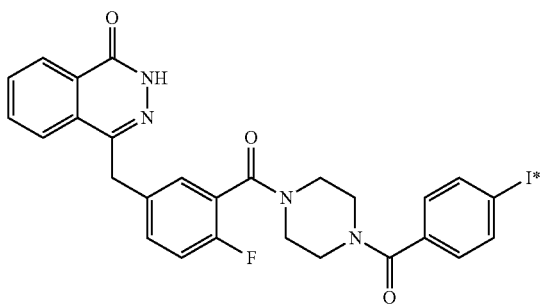

wherein I* is $^{124}$I, or a pharmaceutically acceptable salt thereof.

In some embodiments, a provided radiative emitter is the chemical entity C-2c, that is, the compound:

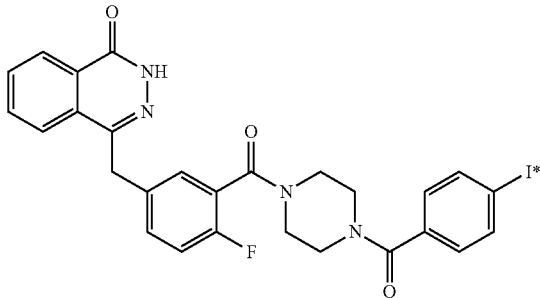

wherein I* is $^{125}$I, or a pharmaceutically acceptable salt thereof.

In some embodiments, a provided radiative emitter is the chemical entity C-2d, that is, the compound:

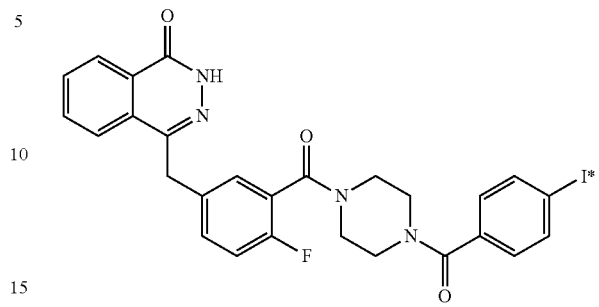

wherein I* is $^{131}$I, or a pharmaceutically acceptable salt thereof.

In some embodiments, a provided radiative emitter is the chemical entity C-2e, that is, the compound:

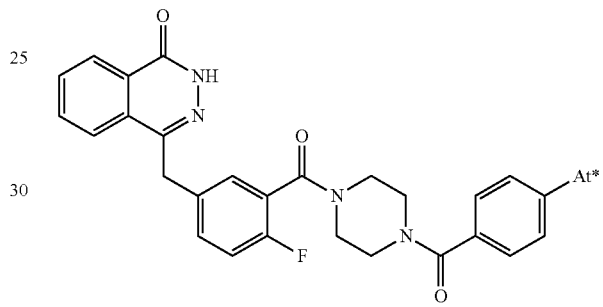

wherein At* is $^{211}$At, or a pharmaceutically acceptable salt thereof.

In some embodiments, a provided radiative emitter is the chemical entity C-2f, that is, the compound:

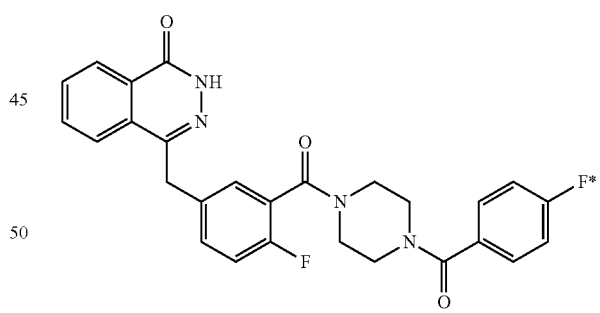

wherein F* is $^{18}$F, or a pharmaceutically acceptable salt thereof.

Unless otherwise explicitly indicated (e.g., by designation of stereochemistry) or clear from context (e.g., as resulting from stereoselective preparation), a structure depicted herein encompasses the compound in any isomeric (e.g., enantiomeric, diastereomeric, and geometric (or conformational)) form; for example, the R and S configurations for each asymmetric center, Z and E double bond isomers, and Z and E conformational isomers. Thus, unless otherwise indicated or clear from context, the present invention encompasses preparation and/or use of single stereochemical isomers as well as enantiomeric, diastereomeric, and/or geometric (or conformational) mixtures of the present chemical entities. Unless otherwise stated or clear from context, all tautomeric forms of the chemical entities of the invention are within the scope of the invention. Additionally, unless otherwise stated or clear from context, structures depicted herein are also meant to include chemical entities that differ only in the presence of one or more isotopically enriched atoms. For example, chemical entities having the present structures including the replacement of hydrogen by deuterium or tritium, or the replacement of a carbon by a $^{13}$C- or $^{14}$C-enriched carbon are within the scope of this invention. Such chemical entities are useful, for example, as analytical tools, as probes in biological assays, or as therapeutic agents in accordance with the present invention.

Definitions and Usage

As used herein, the term "effective amount" means an amount that is sufficient, when administered to a population suffering from or susceptible to a disease, disorder, and/or condition in accordance with a dosing regimen, to treat the disease, disorder, and/or condition. In some embodiments, an effective amount is one that reduces the incidence and/or severity of, and/or delays onset of, one or more symptoms of the disease, disorder, and/or condition. Those of ordinary skill in the art will appreciate that the term "effective amount" does not require successful treatment be achieved in a particular individual. Rather, an effective amount may be that amount that provides a particular desired pharmacological response in a significant number of subjects when administered to patients in need of such treatment. It is specifically understood that particular subjects may, in fact, be "refractory" to an "effective amount." To give but one example, a refractory subject may have a low bioavailability such that clinical efficacy is not obtainable. In some embodiments, reference to an effective amount may be a reference to an amount as measured in one or more specific tissues (e.g., a tissue affected by the disease, disorder or condition) or fluids (e.g., blood, saliva, serum, sweat, tears, urine, etc.). Those skilled in the art will appreciate that, in some embodiments, an effective amount may be formulated and/or administered in a single dose. In some embodiments, an effective amount may be formulated and/or administered in a plurality of doses, for example, as part of a dosing regimen.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the word "about", when used to modify a numeric quantity, means ±8% of the numeric value. Thus, "about 5" means 4.6-5.4, "about 70" means 64-76, etc. For this purpose, percentage values are considered as their nominal quantities, e.g., 5% is treated as 5 rather than 0.05. Thus, "about 5%" means 4.6%-5.4%, "about 70%" means 64%-76%, etc.

Radionuclides as Therapeutic Agents

Auger Emitters

Auger Radiation

Auger radiation was described in 1925 by Pierre Auger. Auger electrons arise from electronic shells of radionuclides when these decay by electron capture. Electron capture processes create inner shell electron vacancies by an electron transfer from this shell into the nucleus. The inner shell electron vacancies are subsequently filled by electron transitions from shells of higher energy, a process that occurs in cascade. The energy difference of these transitions can be released either as photons or as low-energy electrons, the Auger electrons. (F. Bucheggar et al., "Auger radiation targeted into DNA: a therapy perspective", *Eur. J. Nucl. Med. Mol. Imaging* 2006, 33:1352-63.)

Typically, Auger radiation decays produce between 5 and 30 Auger electrons. Depending on the relationship of the electronic shells involved, these transitions are classified into Auger, Coster-Kronig and super-Coster-Kronig processes. The electrons emitted by these three processes are referred to as Auger electrons. (Bucheggar 2006). Auger electrons are of low energy. The small negatively charged low-energy electrons produce multiple ionizations of high linear energy transfer (LET) type (4-26 keV/µm) and consequently have a very short range in biological tissues, typically <0.5 µm. The large majority of Auger electrons have a tissue penetration range of the order of a few nm only. (Bucheggar 2006).

Auger Emitters

A large number of radioisotopes emit some Auger radiation, but the Auger electron emitters receiving the most interest for use in medical applications include $^{125}$I, $^{123}$I and $^{201}$Tl. For these Auger electron emitters, the Auger radiation energy released per decay is significant. In particular, the radioisotope $^{123}$I, though it releases only about 14% of its decay energy in the form of Auger (~3.7%) and IC (internal conversion, ~10.1%) electrons, is considered a good candidate for therapeutic application, owing in part to its half-life of 13.2 hours. (Bucheggar 2006).

Auger Radiation Biology

The double strand DNA helix presents a diameter of 2 nm. In a typical Auger radiation decay, the highest energy deposition occurs in spheres of 1-2 nm. The calculated local energy deposition of an Auger emitter incorporated into DNA would hit both DNA strands with an energy of 1.6 MGy or higher. This radiation energy is therefore largely sufficient to disrupt both DNA strands over distances of several nucleotides. For $^{125}$I or $^{123}$I decays associated with DNA, this translates into a general rule of one decay=one double strand break. The genetic information is lost in these double strand breaks owing to destruction of several nucleotides on both strands. Repair still remains possible but will frequently be erroneous. These features are believed responsible for the high RBE (relative biological efficiency) of Auger radiation when decays occur in close association with DNA. An attractive characteristic of Auger radiation is that it possesses the high toxicity of α radiation when occurring in close vicinity to DNA while being of low toxicity outside the cell nucleus. (Bucheggar 2006).

In addition to the direct effect of Auger electrons on DNA double strands, an indirect radiation effect of Auger energy deposition will occur via production of radicals. The radicals diffuse freely in the intracellular space and can cause further DNA damage. Even a bystander effect by diffusion of radicals through gap junctions has been described. (Bucheggar 2006; see also A. I. Kassis, "Cancer Therapy with Auger Electrons: Are We Almost There?", *J. Nucl. Med.* 2003, 44:1479-81, citing M. A. Walicka et al., *Radiat. Res.* 1998: 149:142-46, M. A. Walicka et al., *Int. J. Radiat. Biol.* 1999, 75:1579-87; M. A. Walicka et al., *Radiat. Res.* 2000, 154: 326-30; M. A. Walicka et al., *Int. J. Radiat. Biol.* 2001, 77:625-30; L. Y. Xue et al., *Proc. Natl. Acad. Sci.* 2002, 99:13765-70).

Therapeutic Applications of Auger Emitters

Assumptions

Due to the short path lengths of most Auger electrons, in contrast to α and β$^-$ radiation, it is generally desirable to deliver them in close proximity to a relevant target. For example, in many embodiments, it is desirable to deliver Auger emitters to individual tumor cells, preferably into the nucleus. It is particularly desirable to deliver Auger emitters in close proximity to, or within, nuclear DNA (L. Bodei et al., *Cancer Biother. Radiopharm.* 2003, 18:861-77) or other radiosensitive target when the Auger emitter can accumulate to a dose sufficient to achieve its intended result (e.g., ultimately, to kill the cell). (L. S. Yasui, "Molecular and cellular effects of Auger emitters: 2008-2011", *Int. J. Radiat. Biol.* 2012, 88(12):864-70).

However, the present invention encompasses the recognition that certain experimental findings over the past decade debunk some basic assumptions that had previously limited the perceived therapeutic potential of Auger electron-emitting radionuclides. (Kassis 2003). For example, toxic effects of low-energy electron emitters had frequently been assumed to result from and depend on covalent binding of the Auger electron-emitting radionuclide to nuclear DNA, but it was subsequently shown that other agents (e.g., steroids, growth factors and DNA intercalators) radiolabeled with such isotopes are also highly toxic to mammalian cells. (Kassis 2003, citing W. D. Bloomer et al., *Int. J. Radiat. Biol.* 1980, 38:197-202; A. I. Kassis et al., *Radiat. Res.* 1989, 118:283-94; R. M. Reilly et al., *J. Nucl. Med.* 2000, 41:429-38; L. S. Yasui et al., *Radiat. Res.* 2001, 155:328-34; L. S. Yasui et al., *Int. J. Radiat. Biol.* 2001, 77:955-62).

Also, it has been postulated that optimal Auger radiation efficacy is obtained when Auger emitters are tightly bound to DNA. Specifically, in order to compare the RBE of different radiation types, the radiation weighting factor ($W_R$) has been introduced. $W_R$ compares the biological efficacy of a given radiation dose of a particular type with that of X-rays, the $W_R$ of X-rays being 1. Many studies assessing the therapeutic efficacy of low-energy electron emitters have been performed with the thymidine analog 5-iodo-2'-deoxy uridine (IdUrd), which can be incorporated into DNA. (Kassis 2003, citing W. D. Bloomer and S. J. Adelstein, *Nature* 1977, 265:620-21; J. Baranowska-Kortylewicz et al., *Int. J. Radiat. Oncol. Biol. Phys.* 1991, 21:1541-51; A. I. Kassis et al., *Acta Oncol.* 2000, 39:731-37). The decay sites of radio-IdUrd, once incorporated into DNA, are in close vicinity to DNA, and double strand breaks occur with a probability of about 1 per decay. The RBE of $^{125}$I-IdUrd and $^{123}$I-IdUrd measured in V79 cells was about 8 and 7, respectively. This means that, for an identical deposition of energy, the Auger radiation of DNA-incorporated $^{125}$I-IdUrd and $^{123}$I-IdUrd would be 8- and 7-fold more efficient compared with X-rays, γ or conventional β⁻ radiation. This biological efficiency of DNA-incorporated $^{125}$I-IdUrd and $^{123}$I-IdUrd would be similar to that of a radiation. It was concluded, however, that nuclear-localized Auger processes that are not directly linked to DNA would develop a $W_R$ only about half that of DNA-associated decays. (Bucheggar 2006).

The present invention appreciates, however, that other studies have demonstrated that, in fact, covalent association is not necessarily required for Auger emitters to maintain sufficient proximity to effectively damage DNA. (Kassis 2003, citing J. C. Sisson et al., *J. Nucl. Biol. Med.* 1991, 35:255-59; L. W. Brady et al., *Int. J. Radiat. Oncol. Biol. Phys.* 1992, 22:225-30; E. R. DeSombre et al. in R. W. Howell et al., eds., *Biophysical aspects of Auger Processes. American Association of Physicists in Medicine Symposium Series No.* 8, Woodbury, N.Y., American Institute of Physics 1992:352-71; L. Snelling et al., *Hybridoma* 1995, 14:111-14; W. A. P. Breeman et al., *Anticancer Res.* 1998, 18:83-89; M. de Jong et al., *Int. J. Cancer* 1998, 75:406-11; M. O. Myers et al., *J. Surg. Res.* 1998, 76:154-58; D. J. Kwekkeboom et al., *J. Nucl. Med.* 1999, 40:762-67; E. R. DeSombre et al., *Acta Oncol.* 2000, 39:659-66; E. T. Janson et al., *J. Nucl. Med.* 2000, 41:1514-18). The present invention provides the recognition that appropriate carrier molecules are available that are internalized into the nuclei of tumor cells and can be used as carriers of Auger electron-emitting radionuclides, including specifically for treatment of diseases, disorders or conditions (e.g., cancer) associated with cell proliferation.

Attempts at Developing Therapeutic Auger Emitters

Although Auger radiation therapy has been a long-standing research goal, its implementation has encountered multiple obstacles, and clinical studies have been very scarce. (F. Bucheggar et al., "Auger radiation targeted into DNA: a therapy perspective", *Eur. J. Nucl. Med. Mol. Imaging* 2006, 33:1352-63). Research has been directed, among other things, at identification and/or development of suitable tumor-selective vehicles for Auger emitters, strategies for repeated application of internal emitters, and/or delivery of Auger radiation to large proportions of all live cancerous cells. (Bucheggar 2006).

The present invention appreciates that, despite the ability of radiolabeled nucleotide analogs such as $^{125}$I- and $^{123}$I-IdUrd, to localize Auger emissions to DNA through their direct incorporation into nascent DNA during the synthesis phase of the cell cycle (Bucheggar 2006, citing A. I. Kassis and S. J. Adelstein, *J. Nucl. Med.* 2005, 46:4S-12S), there are several difficulties associated with radiolabeled nucleotides in therapy. First, they are rapidly degraded but have a limited efficacy time window since they are incorporated into DNA only during the synthesis phase of the cell cycle. For in vivo applications, osmotic pumps delivering radio-IdUrd continuously over several days have been used in an attempt to bypass the problem of the very short circulation time of nucleotides that are rapidly degraded after administration. Such pumps can be cumbersome and expensive to operate. Second, the rate of DNA incorporation of such nucleotide analogs is low, presumably due to rapid catabolism of IdUrd and competition from endogenous thymidine (dThd). Various dThd synthesis inhibition strategies have been employed in an attempt to overcome the low DNA incorporation rate. However, even when these strategies were successful, the increase in incorporation has not been observed to yield the expected increase in therapeutic efficacy of radio-IdUrd. (Bucheggar 2006, citing A. I. Kassis et al., *J. Nucl. Biol. Med.* 1991, 35:167-73). For at least these reasons, nucleotide analogs have not proven to be effective carriers for delivery of Auger emitters to DNA.

Other approaches that have been suggested to localize Auger emitters to DNA, and specifically to achieve localization sufficient to achieve therapeutic benefit (e.g., cell death) include incorporating the Auger emitters into antisense or triplex-forming oligonucleotides that target specific sequences in cellular DNA or mRNA. However, these strategies face a variety of obstacles, including oligonucleotide instability and low rates of uptake into the nuclear target.

Aptamers represent another class of DNA or RNA oligonucleotides with tumor-targeting capabilities. However, in common with other oligonucleotides, the in vivo half-lives of aptamers are generally short. Different stabilization strategies have thus therefore been attempted to overcome this limitation.

Monoclonal antibodies that can be internalized by cells have also been labeled with $^{125}$I and other Auger or low-energy electron emitters. (Bucheggar 2006).

Thus, as can be seen, a number of additional approaches have since been developed to target Auger emitters to tumor cells. See, e.g., L. S. Yasui, "Molecular and cellular effects of Auger emitters: 2008-2011", *Int. J. Radiat. Biol.* 2012, 88(12):864-70. Specific examples include a triple targeting approach used a polymer-based EPR (enhanced permeation and retention) system to target the tumor, pH-controlled release of an intercalator-bound Auger emitter ($^{125}$I-ellipticine) in the slightly acidic tumor tissue or endosome and thirdly, targeting DNA by the radiolabeled-intercalator. (Yasui 2012, citing O. Sedlacek et al., *Bioconj. Chem.* 2011, 22:1194-1201). Another approach used a nanoparticle that contained streptavidin that was linked to three biotinylated components: (1) anti human epidermal growth factor receptor 2 (HER2) antibody (trastuzumab), to improve pharmacokinetics; (2) the tat (transactivator of transcription) peptide, to improve plasma membrane and nuclear transport; and (3) $^{111}$In-labeled antiRIα messenger RNA antisense morpholino (MORF) oligomer. (Yasui 2012, citing X. Liu et al., *J. Nucl. Med.* 2009, 50:582-90). Noting that high levels of androgen receptor (AR) are often indicative of recurrent, advanced or metastatic cancers, and that a high proliferative fraction is found in AR positive tumors, yet another approach used a drug that complexed an androgen with $^{125}$IdU, so that the $^{125}$IdU moiety is released from the androgen when it is in the cell. (Yasui 2012, citing Z. P. Kortylewicz et al., *J. Med. Chem.* 2009, 52:5124-43). Yet another approach, focused on targeting metastasizing cells in the bloodstream with the Auger emitter, utilized $^{125}$I complexed with the DNA intercalator daunorubicin, and the tumor cell-targeting vehicle was a previously reported poly ethylene glycol (PEG)-stabilized epidermal growth factor receptor (EGFR)-targeting liposome that had the EGFR ligand, epidermal growth factor (EGF), present on the surface of the liposome. (Yasui 2012, citing A. Fondell et al., *Eur. J. Nucl. Med. Mol. Imaging* 20107, 37:114-23).

Clinical Studies

Overall, clinical studies with Auger emitters have not met the major goal of efficacy. (Bucheggar 2006). Clinical studies with radio-IdURd have been performed mostly with the aim of measuring and visualizing tumor targeting. (Bucheggar 2006, citing R. G. Blasberg et al., *Cancer Res.* 2000, 60:624-35; A. I. Kassis et al., *J. Nucl. Med.* 1996, 37:19S-22S; G. Mariani et al., *J. Nucl. Med.* 1996, 37:22S-25S; G. Mariani et al., *Acta Oncol.* 1996, 35:941-45; L. Bodei et al., *Cancer Biother. Radiopharm.* 2003, 18:861-77). Multiple injections or prolonged perfusion was not used in these rather preparative clinical approaches. The criterion that tumor therapy with Auger emitters should target a high percentage of all cancerous cells was therefore not met. As a consequence, therapeutic efficacy was generally not observed in these studies. (Bucheggar 2006).

Treatment studies of thyroid cancer and hyperthyroidism have been performed with $^{125}$I. (Bucheggar 2006). The efficacy of $^{125}$I treatment, however, has been limited. It has been hypothesized that the fact that radio-iodine does not enter the nucleus and stays only briefly in the cytoplasm before being deposited in colloidal form might be responsible for the low contribution of Auger effects in treatment. Thus, it has been noted, only a minor portion of the low-energy electrons from $^{125}$I decay in cytoplasm and particularly in colloid can reach the nuclear DNA. (Bucheggar 2006).

Antibodies directed against different tumor-associated antigens might elicit antigen internalization upon binding. Such antibodies have been labeled with $^{125}$I and other Auger or low-energy electron emitters, and therapy studies have been performed in patients. (Bucheggar 2006, citing S. Welt et al., *J. Clin. Oncol.* 1996, 14:1787-97; J. Xiao et al., *Cancer Biother. Radiopharm.* 2005, 20:16-26). Similarly, $^{125}$I-labeled MIBG (meta-iodobenzylguanidine) has been used in an Auger/low-energy electron approach. (Bucheggar 2006, citing J. C. Sisson et al., *Am. J. Clin. Oncol.* 1996, 19:144-48). Therapeutic efficacy with these latter agents was mostly modest. Similar to thyroid treatment with $^{125}$I, the internalizing antibodies do not enter the nucleus. The Auger radiation therefore reaches the nucleus only partially, and its biological efficacy is predicted to be modest, with a $W_R$ of about 1. (Bucheggar 2006).

In sum, the targeting of Auger electron emitters into the nucleus of tumor cells is an appealing approach for systemic radiation therapy. However, multiple obstacles to the successful implementation of such therapies have been recognized. While some of them have been partially overcome, a need remains for a suitable means for delivering such radionuclides preferentially to malignant (versus healthy) cells, and in sufficient concentration for therapeutic efficacy. Additionally, it would be desirable to accomplish this without the need for a secondary factor, such as an osmotic pump, administration of an additional active agent such as a dThd synthesis inhibitor, or a stabilizer.

Alpha Emitters

Alpha (α) particles (i.e., helium nuclei) are effective in killing tumor cells, due to the high linear energy transfer (~100 keV/μm) and short path length (50-100 μm) of α-particles. They can thus focus large amounts of energy over only a few cell diameters. These properties allow for the targeting of specific tumor cells with minimal damage to surrounding healthy tissues. See generally, K. E. Baidoo et al., "Molecular Pathways: Targeted α-Particle Radiation Therapy", *Clin. Cancer Res.* 2013, 19:530-537, incorporated by reference herein in its entirety. Of the α-particle emitters that are currently understood to be medically relevant and are available for potential clinical use ($^{211}$At, $^{212}$Bi, $^{213}$Bi, $^{225}$Ac, $^{223}$Ra, $^{212}$Pb, $^{227}$Th and $^{149}$Tb), $^{211}$At is especially desirable for targeted radiotherapy. $^{211}$At, produced by the cyclotron bombardment of stable $^{209}$Bi with an α-particle beam, has a half-life of 7.2 hours, which is sufficient to allow for the preparation of radiopharmaceuticals and for their delivery to remote sites with a therapeutically effective level of radioactivity. These considerations have led to the investigation of attaching $^{211}$At to various molecules. See, e.g., M. Zalutsky et al., *Curr. Pharm. Des.* 2000, 6:1433-1455; D. Wilbur et al., *Nucl. Med. Biol.* 1993, 20:917-927; D. Wilbur et al., *Bioconjug. Chem.* 2004, 15:203-223; and E. Link, *Hybridoma* 1999, 18:77-82. The toxicity of $^{211}$At-labeled pharmaceuticals to cancer cells has been studied in cell cultures. See, e.g., R. Larsen et al., *Int. J. Radiat. Biol.* 1997, 72:79-90; R. Larsen et al., *Radiat. Res.* 1998, 149:155-162; M. Walicka et al., *Radiat. Res.* 1998, 150:263-268; and M. Zalutsky et al., *Proc. Am. Assoc. Cancer Res.* 2002, 43:481. Treatment of tumors in animal models with these agents has also been performed. R. Larsen et al., *Br. J. Cancer* 1998, 77:1115-1122; P. Garg et al, *Cancer Res.* 1990, 50:3514-3520; H. Andersson et al., *Anticancer Res.* 2001, 21:409-412. A clinical trial with $^{211}$At-labeled monoclonal antibodies has been undertaken at Duke University Medical Center. M. Zalutsky et al., *Neuro-Oncology* 2002, 4(suppl):5103 and M. Zalutsky, *Br. J. Cancer* 2004, 90:1469-1473.

Beta Emitters

Beta (β) decay is a type of radioactive decay in which a beta particle (an electron or positron) is emitted from an atomic nucleus. One source of beta emission is $^{131}$I, which decays with beta (and gamma) emissions with a physical half-life of 8.04 days. The principal beta emission has a mean energy of 191.6 keV. Emission of beta particles has been used to kill tumor cells. For example, now-discontinued Bexxar® (tositumomab and $^{131}$I-tositumomab) was approved in the US for various non-Hodgkin's lymphomas. Similarly, US-approved Zevalin® (ibritumomab tiuxetan) utilizes the beta decay of $^{90}$Y for its utility in the treatment of non-Hodgkin's lymphomas. Thus, beta emission is a demonstrated means of treating cancer. See, e.g., R. L. Wahl, "Tositumomab and $^{131}$I Therapy in Non-Hodgkin's Lymphoma", *J. Nucl. Med.* 2005, 46 Suppl. 1:128S-140S. A compound containing a beta-emitting atom, such as $^{131}$I, so that the compound is a beta-emitter, would have therapeutic utility if it were in sufficient proximity (i.e., the path length) to the tumor cells.

Radionuclides as Diagnostic Agents

The use of certain radionuclides as diagnostic agents, e.g., in Positron Emission Tomography (PET) or Single Photon Emission Computed Tomography (SPECT) is well known. See generally S. L. Pimlott and A. Sutherland, "Molecular tracers for the PET and SPECT imaging of disease", *Chem. Soc. Rev.* 2011, 40:149-162, incorporated by reference herein in its entirety. See also US Patent Appl. Publ. Nos. 2010/0040550 and 2013/0225828.

Imaging agents used for PET are radiolabeled with radionuclides that decay by the emission of a positively charged particle called a positron. On emission from the nucleus, the positron travels a short distance in the surrounding tissue before it annihilates by combining with an electron. On annihilation, the mass of the positron and electron are converted into energy producing two 511 keV γ-rays which are emitted simultaneously at approximately 180° to each other. The pair of γ-rays is detected by surrounding detectors which allow information about the positron annihilation to be recorded. The acquisition of a large number of coincidence events provides data which allow reconstruction into an image with information on the spatial distribution of radioactivity as a function of time, using a technique called electronic collimation. Commonly used radionuclides for PET imaging include $^{11}$C, $^{13}$N, $^{15}$O, $^{18}$F, $^{64}$Cu, $^{68}$Ga, $^{76}$Br and $^{124}$I.

SPECT imaging uses radionuclides that directly emit γ-rays. In SPECT imaging, directional information is obtained by placing a collimator in front of the gamma camera. The collimator defines the angle of incidence of the isotropic γ-rays emitted. Commonly used radionuclides for SPECT imaging include $^{123}$I, $^{131}$I, $^{99m}$Tc, $^{111}$In, $^{67}$Ga and $^{201}$Tl.

PARP1

Poly (ADPribose) polymerase 1 (PARP1) gene, plays an important role for the efficient maintenance of genome integrity. PARP1 is more highly expressed in several types of cancer compared with the equivalent normal tissues. (A. Galia et al., *Eur. J. Histochem.* 56:e9:45-48 (2012). See, e.g., V. Ossovskaya et al., "Upregulation of Poly (ADPribose) polymerase 1 (PARP-1) in Triple-Negative Breast Cancer and Other Primary Human Tumor Types", *Genes Cancer* 1:812-21 (2010); I. Bieche et al., "Poly (ADPribose) polymerase gene expression status and genomic instability in human breast cancer", *Clin. Cancer Res.* 2:1163-76 (1996); F. Rojo et al., "Nuclear PARP-1 protein overexpression is associated with poor overall survival in early breast cancer", *Ann. Oncol.* 23:1156-64 (2012); S. Staibano et al., "Poly (adenosine diphosphate-ribose) polymerase 1 expression in malignant melanomas from photoexposed areas of the head and neck region", *Hum. Pathol.* 36:724-31 (2005), each of which is incorporated by reference herein in its entirety). Overall, the most differences in PARP1 gene expression have been observed in breast, ovarian, endometrial, lung, and skin cancers, and non-Hodgkin's lymphoma. (Galia (2012)). Additionally, the overexpression of PARP1 in particularly apparent in multiple forms of brain malignancies, an effect that is potentiated due to the very limited PARP1 expression in the healthy brain. (Galia (2012); V. N. Barton et al., "PARP1 expression in pediatric central nervous system tumors", *Pediatr. Blood Cancer* 53:1227-30 (2009), incorporated by reference herein in its entirety).

The present invention encompasses the insight that PARP1 is a suitable target for specific localization of radiative emitters for accumulation in cell nuclei, i.e., specifically in nuclei of cells suffering from or susceptible to a disease, disorder or condition, such as cancer, that is associated with cell proliferation. In accordance with the present invention, high tumor expression and low healthy tissue expression of PARP1 renders it particularly useful as a target for radiative emitters useful in the treatment of cancer. Additionally, high tumor expression and low healthy tissue expression of PARP1 renders it particularly useful as a target for a diagnostic agent, e.g., an agent useful in the imaging of tumors.

Targeting PARP Expressing Cells

The study of PARP inhibitors as anti-proliferative therapeutic agents is an active area of research and development, and clinical investigations have been ongoing for the past decade. See generally C. Underhill et al., "A review of PARP Inhibitors: from bench to bedside", *Ann. Oncol.* 2010, doi: 10.1093/annonc/mdq322, incorporated by reference herein in its entirety. PARP inhibitors that have entered al studies either as single agents or in combination include AG014699 (Pfizer), INO-1001 (Inotek/Genentech), AZD2281 (AstraZeneca), ABT-888 (Abbott), BSI-201 (BiPar/Sanofi-Aventis), CEP-9722 (Cephalon), BMN673 (Biomarin) and MK4827 (Merck). The present invention encompasses the insight that a PARP inhibitor can be modified to contain one or more radionuclides such that the PARP inhibitor is a radiative emitter. Such a radiative emitter would be useful as a therapeutic agent, or a diagnostic agent, or both, depending on the identity of the radionuclide(s) employed.

AZD2281 (olaparib) is a PARP inhibitor being investigated in Phase III clinical studies for the treatment of BRCA mutated ovarian cancer. Certain detectable derivatives of olaparib have been reported to bind PARP1, and have use as agents to detect or image cells that overexpress PARP1, such as certain cancer cells. (Intl. Patent Appl. Publ. No. WO 2012/074840, incorporated by reference herein as pertains to the foregoing statement). One such chemical entity,

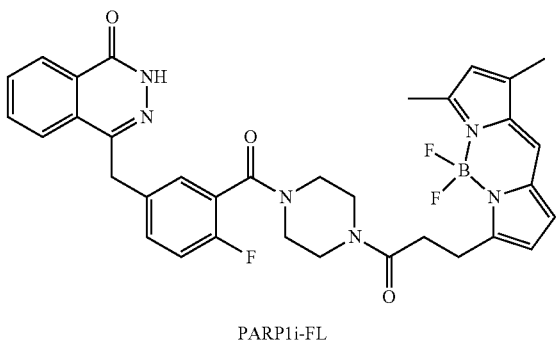

PARP1i-FL has since been further investigated and found to possess suitable properties, e.g., those shown below, to be useful as an agent to detect glioblastomas in vivo, namely, sufficiently low toxicity at concentrations used for imaging, sufficiently high stability in vivo, and sufficiently selective accumulation in glioblastomas, presumably attributable to high PARP1 expression. (T. Reiner et al., unpublished).

| | |
|---|---|
| $EC_{50}$ | 12.2 nM[a] |
| $t_{\alpha 1/2}$ | 1.2 min (73.2%)[c] |
| $t_{\beta 1/2}$ | 88.2 min (26.8%)[c] |
| weighted $t_{1/2}$ | 24.5 min[c] |
| CHI‡ | 72.21[c] |
| $logP_{CHI}$ | 3.0[c] |
| plasma free fraction | 0.7%[b] |

[a]T. Reiner et al., "Imaging Therapeutic PARP Inhibition In Vivo through Bioorthogonally Developed Companion Imaging Agents", Neoplasia 14: 169-177 (2012).
[b]G. M. Thurber et al., "Single-cell and subcellular pharmacokinetic imaging allows insight into drug action in vivo", Nat. Commun. 4: 1504 (2013).
[c]T. Reiner et al., unpublished
‡Chromatographic Hydrophobicity Index For example, binding assays showed that the affinity of PARP1i-FL (12.2 nM) is very close to that of olaparib (5 nM). (K. A. Menear et al., "4-[3-(4-cyclopropanecarbonylpiperazine-1-carbonyl)-4-fluorobenzyl]-2H-phthalazin-1-one: a novel bioavailable inhibitor of poly(ADPribose) polymerase-1", J. Med. Chem. 2008, 51:6581-91, incorporated by reference herein in its entirety). This binding was shown to be rapid and selective to PARP1, similar to parent compound olaparib. (Thurber 2013; Reiner 2012). Additionally, the Chromatographic Hydrophobicity Index (CHI) of 72.21 corresponds to a log $P_{CHI}$ of 3.0, which is comparable to other small molecule drugs, particularly drugs that are available in the central nervous system. (Compare H. Pajouhesh and G. R. Lenz, "Medicinal chemical properties of successful central nervous system drugs", NeuroRx 2005, 2(4):541-53). Moreover, it shows similar toxicity to olaparib in the glioblastoma cell lines U87 and U251 (measured using MTT assay) and a similar reduction in the number of surviving colonies in clonogenic assays using U87 and U251 cells. (T. Reiner et al., unpublished).

Additionally, it was shown on a cellular level that this compound distributes quickly within tumor tissue and efficiently clears from the regions of low PARP1 expression within minutes. (Thurber 2013). Further, ex vivo epifluorescence imaging of PARP1i-FL shows that after an initial clearing phase (0-30 min) that PARP1i-FL is retained in U87 tumors at much higher levels and longer than healthy brain or muscle post intravenous injection. Specifically, at 90 minutes post intravenous injection, the concentration of PARP1i-FL in tumor (mean AU/px=20.49, SEM=3.68) is markedly higher than in muscle (mean AU/px=3.45, SEM=0.45) or brain (mean AU/px=0.13, SEM=0.10). Moreover, uptake of PARP1i-FL by U251 tumors is lower than in U87 tumors, but also markedly higher than that of normal brain and muscle. Western blot analyses show greater expression of PARP1 in tumor tissue compared to normal muscle or brain tissues, correlating to the PARP1i-FL signal. And mice bearing orthotopic tumors show significantly higher uptake of PARP1i-FL than did healthy mice. (T. Reiner et al., unpublished).

The present invention encompasses the insight that a chemical entity having biophysical properties comparable to those of PARP1i-FL would be a suitable delivery vector for certain therapeutic and/or diagnostic radioisotopes. In particular, PARP1i-FL has been shown to accumulate in the nucleus of glioblastoma cells at concentrations of 1-2 µM. (Thurber 2013). This accumulation places it in proximity of tumor cell DNA, the principle target of radiation therapy. In order spare a healthy cell next to a malignant cell, a radiotherapeutic should have an energy deposition radius smaller than that of the nucleus itself. For example, Auger Electron emitters dissipate their energies within nanometers of the decay site. (A. I. Kassis, "Cancer Therapy with Auger Electrons: Are We Almost There?", J. Nucl. Med. 44:1479-81 (2003); J. L. Humm and D. E. Charlton, "A new calculational method to assess the therapeutic potential of Auger electron emission", Int. J. Radiat. Oncol. Biol. Phys. 17:351-60 (1989)). Thus, the present invention further encompasses the insight that a chemical entity both having biophysical properties comparable to those of PARP1i-FL and containing a radioisotope such that the chemical entity is an Auger Electron emitter, e.g., $^{123}$I or $^{125}$I, could serve a therapeutic agent with greater selectivity for malignant versus healthy cells.

Biophysical Properties

Certain biophysical properties of cold (i.e., non-radioactive) analogs of exemplary radiative emitters of formula (I) are shown in Table 2, below. These properties were measured according to the procedures of Example 2.

TABLE 2

| Compound* | $IC_{50}$ (nM)† | CHI‡ | $logP_{CHI}$ | % plasma free fraction |
|---|---|---|---|---|
| c-1 ($^{127}$I) | 11 ± 3 | 59.6 | 2.3 | 9.6 ± 1.5% |
| c-2 ($^{127}$I) | 9 ± 2 | 59.6 | 2.3 | 11.5 ± 0.1% |
| c-3 ($^{127}$I) | 34 ± 3 | 66.7 | 2.7 | 7.0 ± 0.1% |
| c-4 ($^{127}$I) | 74 ± 5 | 66.7 | 2.7 | 5.0 ± 0.3% |
| c-5 ($^{127}$I) | 107 ± 4 | 71.6 | 3.0 | 7.8 ± 1.4% |
| c-6 ($^{127}$I) | 47 ± 5 | 71.6 | 3.0 | 4.7 ± 0.5% |

*Compounds c-1 to c-6 have the same structure as compounds C-1 to C-6, above, but contain the indicated isotope in place of the radiohalide.
†Measured against PARP1
‡Chromatographic Hydrophobicity Index Based on these properties, chemical entities C-1a through C-6a are considered to be useful as therapeutic agents. The foregoing characteristics indicate that these chemical entities will exhibit relevant pharmacokinetic behavior comparable to PARP1i-FL, namely, that they will accumulate in the nuclei of malignant (e.g., glioblastoma) cells and will be retained at higher levels and longer than in healthy brain or muscle. For example, the CHI and log $P_{CHI}$ values, while higher than those reported for olaparib (34.1 and 0.8, respectively), are adequate for crossing the blood brain barrier for application in brain disease. These compounds also showed relatively high plasma protein binding. Accordingly, as Auger emitters, chemical entities C-1a through C-6a are useful for the treatment of cancer. Additionally, as noted above, $^{123}$I can also be used as a SPECT imaging agent. Accordingly, chemical entities C-1a through C-6a are useful as diagnostic agents.

Analogous compounds containing other isotopes of iodine are expected to have the same relevant biophysical properties, and therefore are useful as described above. Thus, $^{124}$I-containing compounds C-1b to C-6b are useful as diagnostic agents, e.g., in PET imaging; $^{125}$I-containing compounds C-1c to C-6c are Auger electron emitters and useful in the treatment of cancer; $^{131}$I-containing compounds C-1d to C-6d are beta emitters and useful in the treatment of cancer, and are useful as diagnostic agents, e.g., in SPECT imaging; and $^{211}$At-containing compounds C-1e to C-6e are alpha emitters and useful in the treatment of cancer.

Similarly, other PARP-inhibiting compounds containing one or more radiohalides, e.g., $^{123}$I, $^{124}$I, $^{125}$I, $^{131}$I or $^{211}$At are useful in the treatment and/or diagnosis of proliferative disorders such as cancer. In some embodiments, the compound inhibits PARP1 with an $IC_{50}$ of about 500 nM or less. In some embodiments, the compound inhibits PARP1 with an IC$_{50}$ of about 250 nM or less. In some embodiments, the compound inhibits PARP1 with an IC$_{50}$ of about 100 nM or less. In some embodiments, the compound is radiohalide-labeled AG014699, INO-1001, AZD2281, ABT-888, BSI-201, CEP-9722, BMN673 or MK4827.

Certain biophysical properties of another exemplary radiative emitter of formula (I), and a cold analog thereof, are shown in Table 3, below. These properties were measured according to the procedures of Example 2.

TABLE 3

| Compound | IC$_{50}$ (nM)† | CHI‡ | logP$_{CHI}$ | logP$_{O/W}$ | Plasma protein binding |
|---|---|---|---|---|---|
| c-2 ($^{19}$F) | 2.8 ± 1.1 | 57.5 | 2.15 ± 0.41 | | 63.9 ± 12.6% |
| C-2f ($^{18}$F) | | | | 1.76 ± 0.18 | |

†Measured against PARP1
‡Chromatographic Hydrophobicity Index

As shown, the IC$_{50}$ of c-2 ($^{19}$F) is on par with that of olaparib (5 nM). Calculated from its chemical hydrophobicity index, the log P$_{CHI}$ of c-2 ($^{19}$F) was determined to be 2.15±0.41, which is concordant with measuring the octanol/water partition coefficient of C-2f ($^{18}$F), determined to be 1.76±0.18. The log P of c-2 ($^{19}$F) was higher than for olaparib (CHI=34.1, log P$_{CHI}$=0.8), but the molecules had comparable plasma protein binding (64% and 65% for c-2 ($^{19}$F) and olaparib, respectively). Based on these properties, chemical entity C-2f ($^{18}$F) is considered to be useful as a diagnostic agent, e.g., in PET imaging. $^{18}$F-containing compounds C-1f and C-3f to C-6f are expected to have similar relevant biophysical properties, and therefore are also useful as diagnostic agents, e.g., in PET imaging.

In addition, as noted above, PARP1i-FL possesses suitable biophysical properties to be useful as an agent for in vivo detection of malignant (e.g., glioblastoma) cells by fluorescence. The present invention encompasses the insight that $^{18}$F-PARP1i-FL:

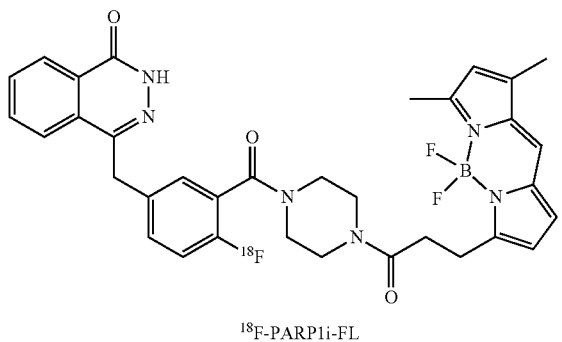

$^{18}$F-PARP1i-FL being structurally identical to PARP1i-FL, will possess suitable biophysical properties to be useful as an agent for detection of malignant (e.g., glioblastoma) not only by fluorescence but also by PET, due to its $^{18}$F atom. This multi-modal chemical entity has utility in both in vivo and ex vivo settings. For example, PET imaging can be used to detect PARP1-expressing tumors in whole-body studies. Following the PET scan, lesions can be biopsied and the findings of the PET scan can be validated by comparing ex vivo fluorescent images with immunohistochemistry of PARP1. This also allows studies of the heterogeneity of PARP1 expression within a tumor.

Similarly, the present invention encompasses the insight that $^{18}$F-PARP1i-FL(2):

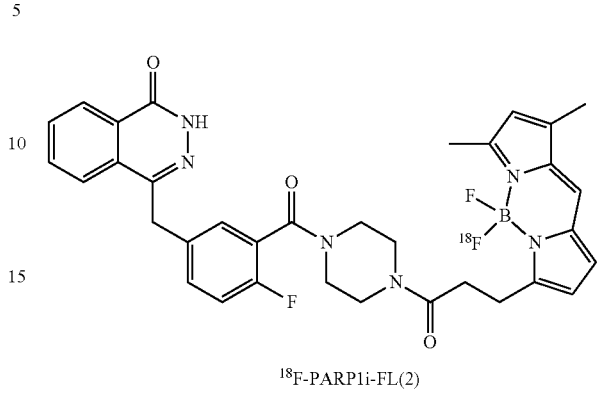

$^{18}$F-PARP1i-FL(2)

will possess the same multi-modal imaging utility as $^{18}$F-PARP1i-FL. $^{18}$F-PARP1i-FL(2) can be synthesized from PARP1i-FL via $^{18}$F/$^{19}$F exchange in the presence of SnCl$_4$. See G. Carlucci et al., "Dual-Modality Optical/PET Imaging of PARP1 in Glioblastoma", Mol. Imaging Biol. 2015, DOI: 10.1007/s11307-015-0858-0.

Competition Assays

To demonstrate the preferential binding of exemplary chemical entities of formula (I) to PARP1, competition assays were performed as described in Example 3.

Figure 3:
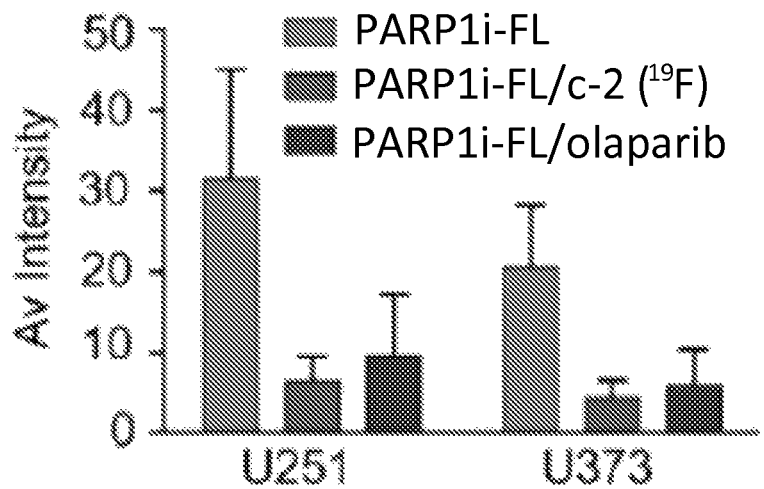
FIG. 3 illustrates the reduction in fluorescence intensity attributable to the competitive inhibition of PARP1-iFL uptake in U251 MG and U373 MG cells by compound c-2 ($^{19}$F), determined as described in Example 3.2.2.

In vitro competition assays were performed with cold compounds c-1 ($^{127}$I) to c-6 ($^{127}$I)—whose binding is expected to be substantially similar or identical to the respective corresponding radiative emitters C-1 to C-6—and the fluorescent imaging agent, PARP1i-FL (Example 3.2.1). PARP1i-FL alone led to strong nuclear fluorescence, where the agent was retained by PARP1. The reduction in fluorescent signal in the presence of each compound confirmed their ability to diffuse into the nucleus of the cell and bind PARP1 (confocal images not shown). When PARP1i-FL was added to cells that were co-treated with any of compounds c-1 ($^{127}$I) to c-6 ($^{127}$I), a reduction in fluorescence signal between 76±6% and 67±13% was seen (see FIG. 3). This was similar to results obtained for olaparib, where co-treatment resulted in a reduction of PARP1i-FL uptake by 73±10% (see FIG. 3).

Similar competition assays were performed using cold compound c-2 ($^{19}$F) in U251 MG and U373 MG cells (Example 3.2.2). In the presence of olaparib, binding sites for PARP1i-FL were occupied, and the observed fluorescence is reduced by 69.6%±22.3% and 71.2%±20.0% for U251 MG and U373 MG cells, respectively (see FIG. 3). Similarly, c-2 ($^{19}$F) was able to compete for the same binding sites as PARP1i-FL resulting in a reduction of fluorescence intensity in the nucleus by 80.0%±10.8% and 78.8%±10.4% for U251 MG and U373 MG cells, respectively (see FIG. 3).

The binding characteristics of cold compound c-2 ($^{127}$I) were explored ex vivo by epifluorescence imaging of U87 MG tumor tissue (Example 3.2.3). The tissue was obtained from mice that were injected with c-2 ($^{127}$I), before receiving an injection of PARP1i-FL. A second group received PARP1i-FL alone, without injection of c-2 ($^{127}$I). Mice receiving both agents showed a 78±4% lower tumor fluorescence (images not shown), compared with the mice receiving just PARP1i-FL (4.53×10$^7$±0.81×10$^7$ and 2.03×

Figure 4:
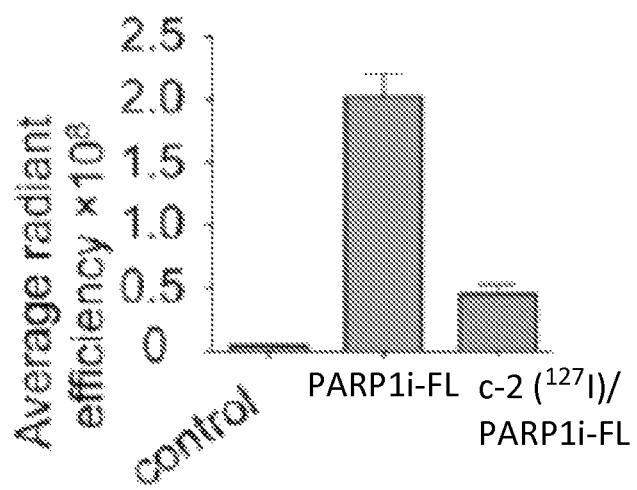
FIG. 4 illustrates the reduction in fluorescence intensity attributable to the competitive inhibition of PARP1-iFL uptake in U87 MG subcutaneous tumors by compound c-2 ($^{127}$I), determined as described in Example 3.2.3.

$10^8 \pm 1.84 \times 10^7$ average radiant efficiency, respectively; see FIG. 4). A control group received just PBS, and tumors from these mice did not show significant fluorescence (0.42× $10^6 \pm 0.07 \times 10^6$ average radiant efficiency; see FIG. 4). Similar results could be seen using confocal microscopy, where tumors from mice injected with PARP1i-FL show clear nuclear uptake in U87 MG tumors, whereas there was a significant decrease in uptake for mice which also received c-2 ($^{127}$I), similar to what was observed for the control tumors (confocal images not shown).

In Vivo Pharmacokinetics of Exemplary Radiative Emitters

Certain pharmacokinetic properties of exemplary radiative emitters of formula (I) were measured in vivo as described in Example 3.

In healthy athymic nude mice the compound C-2d ($^{131}$I) was quickly cleared from the blood, similar to the compounds reported in C. P. Irwin et al., "PARPi-FL—a Fluorescent PARP1 Inhibitor for Glioblastoma Imaging", *Neoplasia* 2014, 16:432-40; T. Reiner et al., "Imaging Therapeutic PARP Inhibition In vivo through Bioorthogonally Developed Companion Imaging Agents", *Neoplasia* 2012, 14:169-77; and G. M. Thurber et al., "Single-cell and subcellular pharmacokinetic imaging allows insight into drug action in vivo", *Nat Commun.* 2013, 4:1504. The weighted blood half-life of C-2d (Example 3.1.1) was 17.1 min (alpha blood half-life of 14.3 min (96.25%) and beta blood half-life of 94.6 min (3.75%)). Additionally, in vitro blood stability studies confirmed the stability of the compound over the course of 60 minutes (Example 3.1.3), and over the course of 120 minutes.

Biodistribution of C-2d ($^{131}$I) was analyzed after administration of the compound (24±5 µCO in U87 MG and U251 MG tumor bearing mice (Example 3.3.1). Results are shown in Tables B5 and B7, below. At 2 h post intravenous injection in U87 MG tumor bearing mice, uptake in tumor, muscle and brain was 0.17±0.06% ID/g, 0.04±0.02% ID/g and 0.007±0.002% ID/g, respectively, yielding ratios of both tumor:muscle (about 4:1 to 5:1) and tumor:brain (about 24:1 to 25:1) that indicate potential clinical value, e.g., in imaging. Similarly, at 2 h post intravenous injection in U251 MG tumor bearing mice, uptake in tumor, muscle and brain was 0.43±0.06% ID/g, 0.03±0.01% ID/g and 0.011±0.003% ID/g, respectively, yielding ratios of both tumor:muscle (about 13:1 to 15:1, e.g., about 14:1) and tumor:brain (about 39:1 to 43:1, e.g., about 40:1) that indicate potential clinical value, e.g., in imaging. The high uptake observed in the liver is common for intravenously administered small molecules that are excreted hepatobiliary.

TABLE B5

| C-2d ($^{131}$I) in U87 MG | | |
| --- | --- | --- |
| Organ | 2 h (% ID/g) | 2 h (S.D.) |
| Blood | 0.90 | 0.65 |
| Tumor | 0.17 | 0.06 |
| Muscle | 0.039 | 0.020 |
| Bone | 0.044 | 0.005 |
| Liver | 1.02 | 0.39 |
| Spleen | 0.15 | 0.08 |
| Kidneys | 0.35 | 0.10 |
| Heart | 0.10 | 0.02 |
| Lung | 0.28 | 0.19 |
| Pancreas | 0.42 | 0.31 |
| Brain | 0.007 | 0.002 |
| Skin | 0.091 | 0.061 |
| Small intestine | 7.16 | 5.45 |
| Large intestine | 0.94 | 0.66 |
| Stomach | 1.90 | 0.97 |

TABLE B5-continued

| C-2d ($^{131}$I) in U87 MG | | |
| --- | --- | --- |
| Organ | 2 h (% ID/g) | 2 h (S.D.) |
| Tail | 0.45 | 0.14 |
| Thyroid | 0.14 | 0.03 |
| Feces | 3.75 | 2.05 |

TABLE B7

| C-2d ($^{131}$I) in U251 MG | | |
| --- | --- | --- |
| Organ | % ID/g | S.D. |
| Blood | 0.27 | 0.06 |
| Tumor | 0.43 | 0.06 |
| Muscle | 0.03 | 0.01 |
| Bone | 0.07 | 0.04 |
| Liver | 2.34 | 0.57 |
| Spleen | 0.40 | 0.10 |
| Kidneys | 0.61 | 0.17 |
| Heart | 0.16 | 0.06 |
| Lung | 0.28 | 0.12 |
| Pancreas | 0.15 | 0.05 |
| Brain | 0.01 | 0.00 |
| Skin | 0.25 | 0.09 |
| Small intestine | 11.70 | 11.40 |
| Large intestine | 1.26 | 1.15 |
| Stomach | 0.88 | 0.47 |
| Tail | 0.60 | 0.35 |
| Thyroid | 0.24 | 0.06 |
| Feces | 4.34 | 1.22 |

The blood half-life of C-2f ($^{18}$F) was determined in athymic nude mice, which received the compound via tail vein injection. The compound was cleared rather quickly, similar to the compounds reported in T. Reiner et al., "Imaging Therapeutic PARP Inhibition In vivo through Bioorthogonally Developed Companion Imaging Agents", *Neoplasia* 2012, 14:169-77; G. Carlucci et al., "Dual-Modality Optical/PET Imaging of PARP1 in Glioblastoma", *Mol. Imaging Biol.* 2015, DOI: 10.1007/s11307-015-0858-0; and G. M. Thurber et al., "Single-cell and subcellular pharmacokinetic imaging allows insight into drug action in vivo", *Nat Commun.* 2013, 4:1504. The weighted blood half-life (Example 3.1.2) was 5.6 minutes (alpha blood half-life of 1.27 minutes (85.51%) and beta blood half-life of 31.14 minutes (14.49%)). Additionally, in vitro blood stability studies (Example 3.1.4) indicated excellent stability and potentially low bone uptake of the compound for in vivo applications.

Biodistribution of C-2f ($^{18}$F) was analyzed after administration of the compound in U251 MG tumor bearing mice (Example 3.3.2). Results are shown in Table B8, below. At 2 h post intravenous injection, uptake in tumor, muscle and brain was 1.82±0.21% ID/g, 0.37±0.09% ID/g and 0.04±0.01% ID/g, respectively, yielding ratios of both tumor:muscle (about 4:1 to 6:1, e.g., about 5:1) and tumor:brain (about 45:1 to 55:1, e.g., about 45:1, about 50:1, about 55:1) that indicate potential clinical value, e.g., in imaging. C-2f ($^{18}$F) was rapidly washed out from most organs, resulting in a high tumor-to-normal tissue contrast at 2 hours post-injection for subcutaneous and orthotopic tumors. (It should be noted that the % ID/g values in Table B8, below, and the various Tables B throughout the application, reflect a number of significant digits generated by software utilized in the analysis. Using the raw data and averaging from multiple experiments can lead to differences in the ratio calculated. For example, the tumor:brain ratio calculated as 1.82/0.04=45.5:1, but the ratio calculated using the raw (unrounded) numbers yields a ratio of 54.9:1. However, one skilled in the art will readily appreciate that the apparent discrepancy is inconsequential in the context of the present invention: both values support clinical utility of the compounds.) High uptake was also observed in the hepatobiliary system (liver, small intestine, large intestine), lymph node and spleen. Highly selective uptake in these organs is based on their rather high PARP1 expression, shown in immunohistochemical stainings, which were obtained in non-tumor-bearing mice (images not shown).

TABLE B8

C-2f ($^{18}$F) in U251 MG

| Organ | % ID/g | S.D. |
|---|---|---|
| Blood | 0.41 | 0.09 |
| Tumor | 1.82 | 0.21 |
| Muscle | 0.37 | 0.09 |
| Bone | 1.21 | 0.24 |
| Liver | 3.98 | 0.56 |
| Spleen | 4.04 | 1.23 |
| Kidney | 1.17 | 0.46 |
| Heart | 0.30 | 0.08 |
| Lung | 0.44 | 0.11 |
| Pancreas | 1.71 | 0.41 |
| Brain | 0.04 | 0.01 |
| Small intestine | 2.94 | 0.91 |
| Large intestine | 2.24 | 0.59 |
| Stomach | 0.73 | 0.3 |
| Lymph nodes | 2.80 | 0.51 |

In Vivo Imaging and Autoradiography Using Exemplary Radiative Emitters

Illustrative imaging studies using exemplary radiative emitters of formula (I) were performed as described in Example 4 and demonstrate their usefulness in in vivo applications.

Figure 5A:
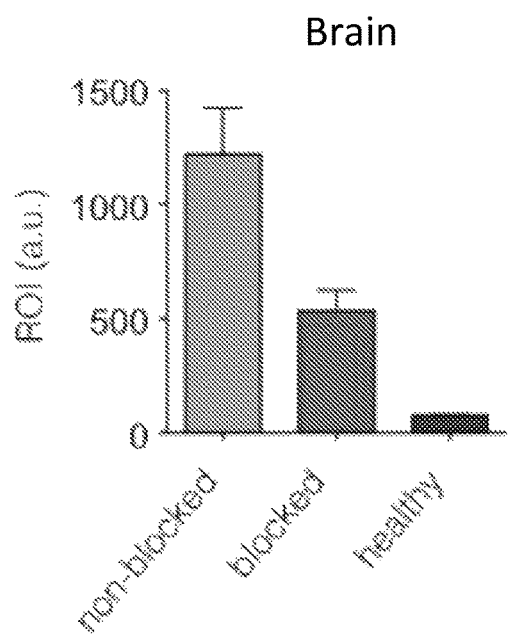
FIG. 5 illustrates the quantification of C-2d ($^{131}$I) uptake in brain (FIG. 5A) or muscle (FIG. 5B) in mice bearing orthotopic U251 MG xenografts, determined as described in Example 4.2.1.
Figure 5B:
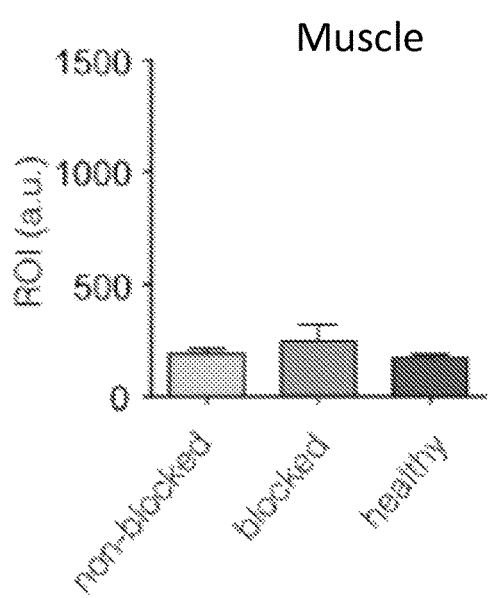

For example, SPECT/CT studies were performed using C-2d ($^{131}$I) in athymic nude mice bearing orthotopic U251 MG xenografts (Example 4.1.1). In images acquired 90 min post injection of the C-2d, the orthotopic tumor could be readily visualized, with uptake of the compound in the right hemisphere of the brain, where the tumor was implanted (image not shown). This data is also supported by ex vivo autoradiography (Example 4.2.1). Histological sections of orthotopic U251 MG tumors showed a clear delineation of tumor tissue with C-2d, but not for mice where PARP1 was saturated with a pre-injection of the non-labeled PARP1 inhibitor olaparib (image not shown). The signal intensity of C-2d in tumor tissue of mice that received no olaparib was 15.7-fold higher than healthy brain tissue (see FIG. 5A) and 6.2-fold higher than muscle tissue (see FIG. 5B), corroborating the SPECT data. There was a 65% reduction in intensity of the autoradiography signal in tumor tissue for mice that had been treated with olaparib (1222±203 and 536±87 AU for mice without and with olaparib treatment, respectively (see FIG. 5A), further showing the specificity of the compound. In contrast, the intensity of the muscle did not undergo statistically significant changes (192±20 and 248±72 AU for mice without and with olaparib treatment, respectively (see FIG. 5B).

PET/CT data was obtained after intravenous injection of C-2b ($^{124}$I) (180-230 μCi, 110-170 mCi/μmol) in athymic nude mice bearing orthotopic U251 MG xenografts (Example 4.2.2). Similar to SPECT/CT, orthotopic U251 MG xenografts were clearly visualized noninvasively, whereas healthy mice showed negligible uptake of the compound (images not shown). Ex vivo biodistribution data with C-2d ($^{131}$I) (see above) corroborated the PET/CT data.

Figure 6A:
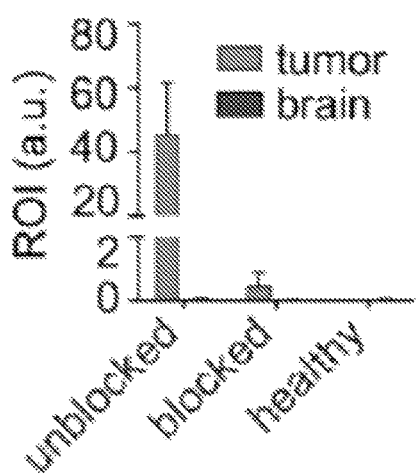
FIG. 6 illustrates the quantification of C-2f ($^{18}$F) uptake with and without olaparib in orthotopic U251 MG tumor bearing mice in tumor and brain (FIG. 6A) or muscle (FIG. 6B), determined as described in Example 4.2.2.
Figure 6B:
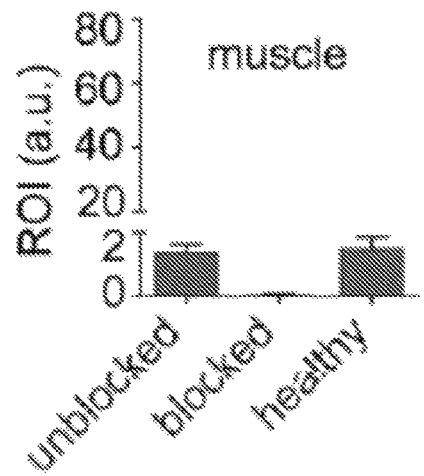

Autoradiographic and PET studies were performed using C-2f ($^{18}$F) an orthotopic U251 MG tumor bearing mice. In order to assess the alignment of C-2f retention and PARP1 expression on a microscopic level in vivo, tumor-bearing mice were injected with C-2f and autoradiography was performed (Example 4.2.2). Using histology to localize the tumor regions of the brain, the autoradiographic analysis revealed significantly higher retention of C-2f inside orthotopic tumor tissue than in healthy surrounding brain: 46.66±14.94 AU and 0.06±0.02 AU for orthotopic tumor and surrounding brain, respectively (see FIG. 6A). Similarly, preinjection of olaparib and hence saturation of PARP1 binding sites lead to almost quantitative reduction of C-2f: 99%, 0.44±0.41 AU and 0.03±0.01 AU for orthotopic tumor and surrounding brain, respectively (see FIG. 6A). The uptake of C-2f in orthotopic tumor tissue was distinctly higher than in muscle: 1.36±0.21 AU and 1.50±0.31 AU for muscle tissue in tumor-bearing and healthy mice, respectively (see FIGS. 6A and 6B).

Figures 7A, 7B:
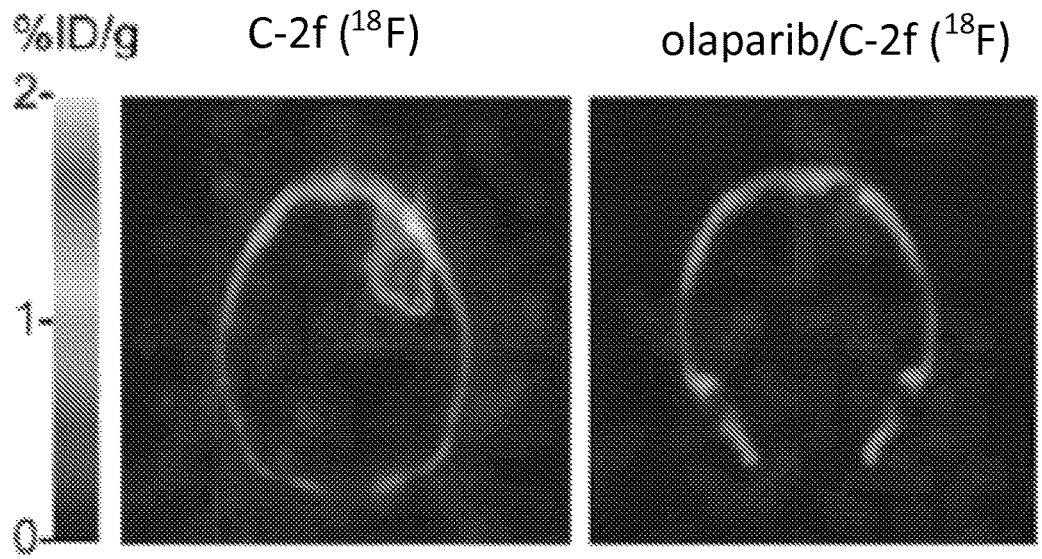
FIG. 7 shows fused PET/CT coronal images of a brain orthotopic U251 MG tumor bearing mouse acquired at 2 h post injection of C-2f (FIG. 7A) or olaparib (500-fold excess) followed by C-2f (FIG. 7B), acquired as described in Example 4.1.3.
Figure 8:
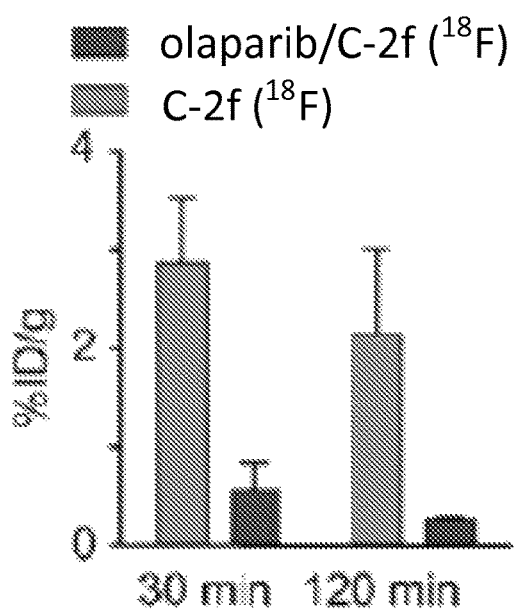
FIG. 8 shows PET quantification of C-2f and olaparib/C-2f in U251 MG tumors from images acquired at 30 min and 2 h post-injection (n=10), determined as described in Example 4.1.3.
Figures 9A, 9B, 9C, 9D, 9E, 9F:
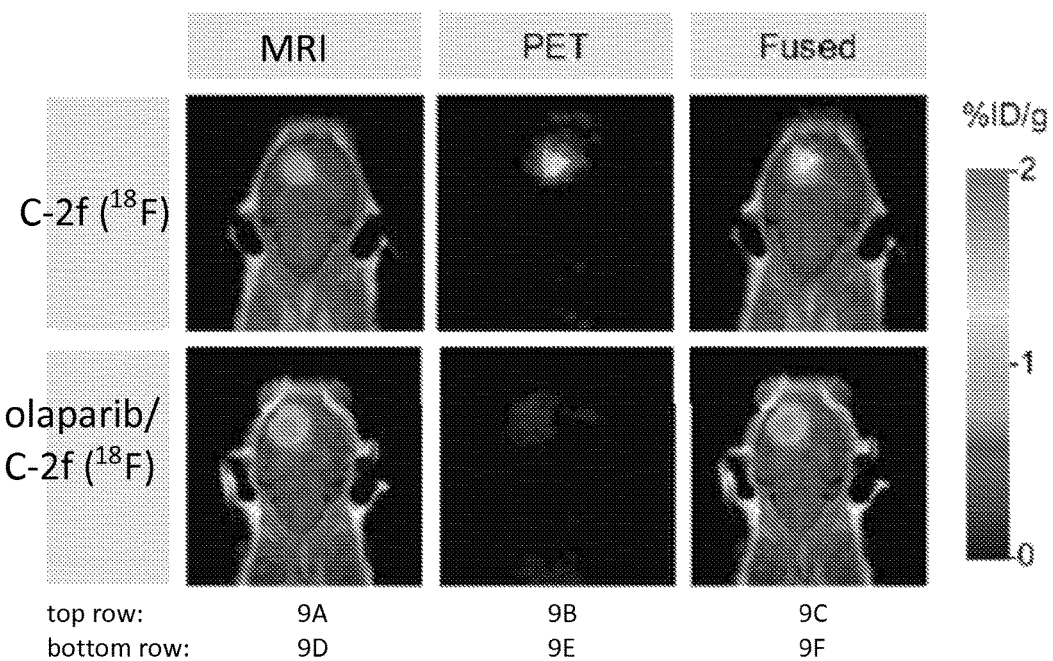
FIG. 9 shows coronal views of C-2f PET images, contrast-enhanced MRI, and fused PET/MRI of orthotopic U251 MG tumor-bearing mice, acquired as described in Example 4.1.4. Top row (left to right, FIGS. 9A-9C): MRI (FIG. 9A), PET (FIG. 9B), and co-registered PET/MRI (FIG. 9C) for a mouse receiving only C-2f. Bottom row (left to right, FIGS. 9D-9F): MRI (FIG. 9D), PET (FIG. 9E), and co-registered PET/MRI (FIG. 9F) for a mouse receiving C-2f after a 500-fold excess of olaparib.

Imaging studies using small animal PET/CT and PET/MRI scanners (Examples 4.1.3 and 4.1.4, respectively) were performed to demonstrate the accuracy and selectivity of non-invasive glioblastoma delineation with C-2f ($^{18}$F). FIG. 7 shows PET/CT images of axial brain slices, obtained 120 minutes after injection, of tumor-bearing animals that received either only C-2f (FIG. 7A) or olaparib/C-2f (FIG. 7B). As shown in FIG. 8, for animals receiving only C-2f, the retained activity (2.15±0.79% ID/g) was eight-fold higher than for animals that received both olaparib and C-2f (0.28±0.01% ID/g. PET/MRI also confirmed uptake of C-2f in the tumor tissue, which was identified on post Gadolinium contrast, $T_1$-weighted images (FIGS. 9A-9F).

Syntheses

Chemical entities of formula (I) can be synthesized according to Scheme 1.

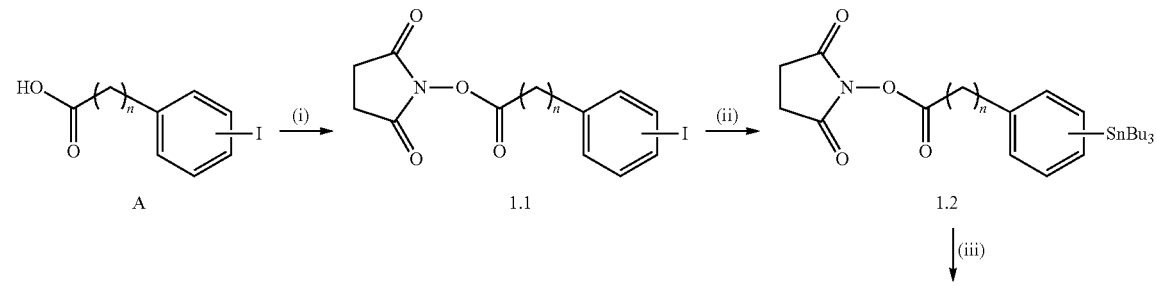

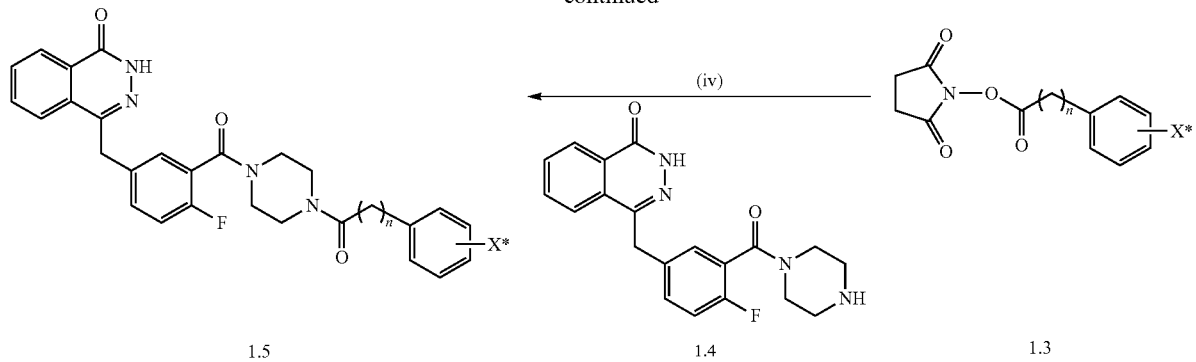

$X^* = {}^{123}I, {}^{124}I, {}^{125}I, {}^{131}I \text{ or } {}^{211}At$
(i) EDC, NSH, CH$_2$Cl$_2$, 40° C., N$_2$
(ii) Sn$_2$Bu$_6$, Pd(PPh$_3$)$_4$, N$_2$, MW, 150° C., toluene, 60 min.
(iii) {${}^{123}I, {}^{124}I, {}^{125}I, {}^{131}I, {}^{211}At$}, Chloramine T, 10 min, RT
(iv) HBTU, Et$_3$N, AcN, 3 h, RT Compound 1.1 can be synthesized as described in, e.g., T. A. Shell, "Selective targeting of DNA for cleavage within DNA-histone assemblies by a spermine-[CpW(CO)$_3$Ph]$_2$ conjugate", Org. Biomol. Chem. 2005, 3:3091-3093, incorporated by reference herein for the referenced synthesis, from the appropriate intermediate A (m-iodo or p-iodo benzoic, phenylacetic or 3-phenylpropanoic acid) in the presence of N-hydroxysuccinimide (NHS) and N-(3-dimethylaminopropyl)-N'-ethylcarbodiimide hydrochloride (EDC). Stannylation to form 1.2, followed by halodestannylation carried out in presence of catalytic amounts of Pd(0), yields radiohalide-labeled 1.3. See generally R. Bolton, "Radiohalogen incorporation into organic systems", J. Label. Compd. Radiopharm. 2002, 45:485-528, e.g., pp. 505-517; and D. S. Wilbur, "Radiohalogenation of Proteins: An Overview of Radionuclides, Labeling Methods, and Reagents For Conjugate Labeling", Bioconjug. Chem. 1992, 3:433-470, each of which is incorporated by reference herein in its entirety. Compound 1.4 can be synthesized according to the method described in K. A. Menear et al., "4-[3-(4 Cyclopropanecarbonylpiperazine-1-carbonyl)-4-fluorobenzyl]-2H-phthalazin-1-one: A Novel Bioavailable Inhibitor of Poly(ADP-ribose) Polymerase-1", J. Med. Chem. 2008, 51:6581-6591, incorporated by reference herein for the referenced synthesis. Compound 1.5 can be obtained from coupling 1.3 with 1.4 using, e.g., HBTU (N,N,N',N'-tetramethyl-O-(1H-benzotriazol-1-yl)uronium hexafluorophosphate) and Et$_3$N (triethylamine) in DMF (dimethylformamide) or AcN (acetonitrile) at room temperature.

${}^{18}$F-PARP1i-FL can be synthesized according to Scheme 2.

Scheme 2

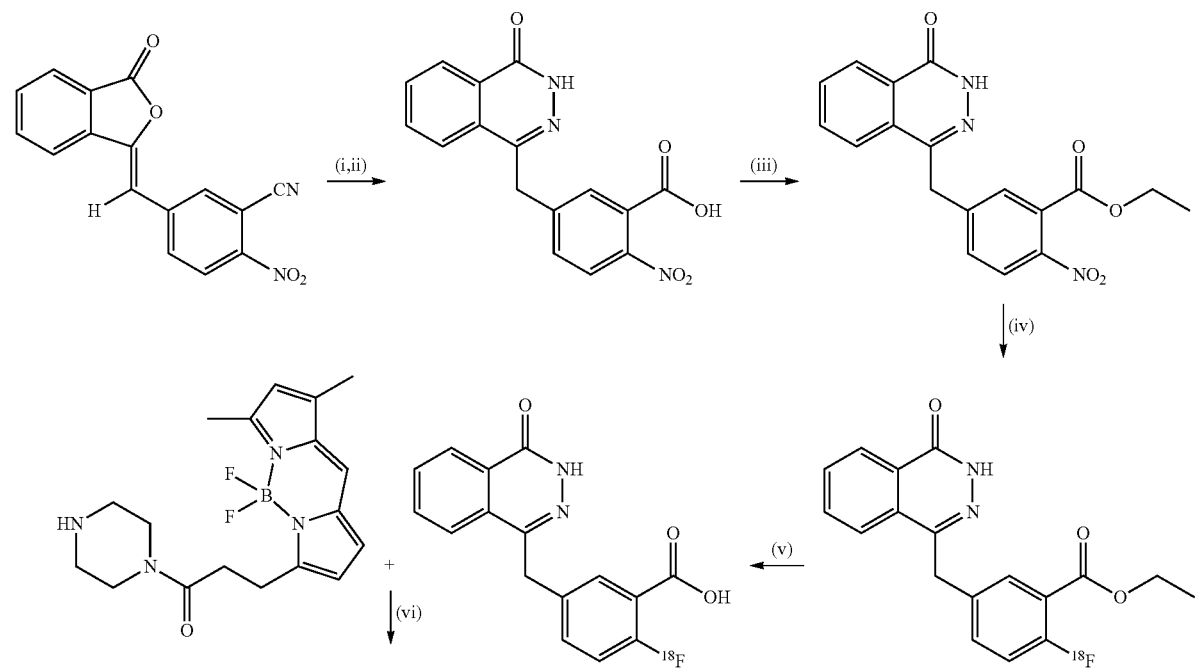

-continued

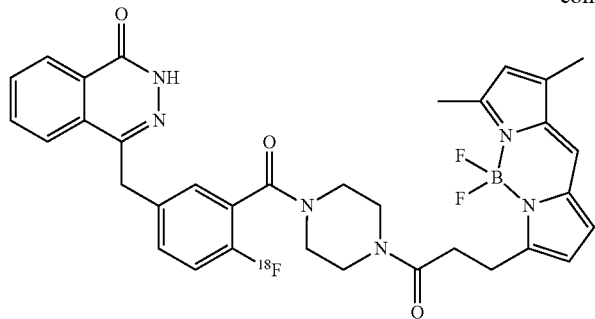

(i) (a) NaOH (aq), THF, 72 h, 100° C.; (b) HCl (2N); (ii) NH$_2$NH$_2$·H$_2$O, 3 h, reflux; (iii) CDI, Et$_3$N, DCM, 6 h, RT;
(iv) [$^{18}$F]KF/K$_{222}$, DMF, 130° C., 15 min; (v) DMF, 130° C., 15 min, MeOH, NaOH 10 min, followed by
HPLC (15 min); (vi) HBTU, DIPEA, DCM, 10 min, RT, followed by HPLC (15 min)

Chemical entities C-1f to C-6f can also be synthesized according to Scheme 3.

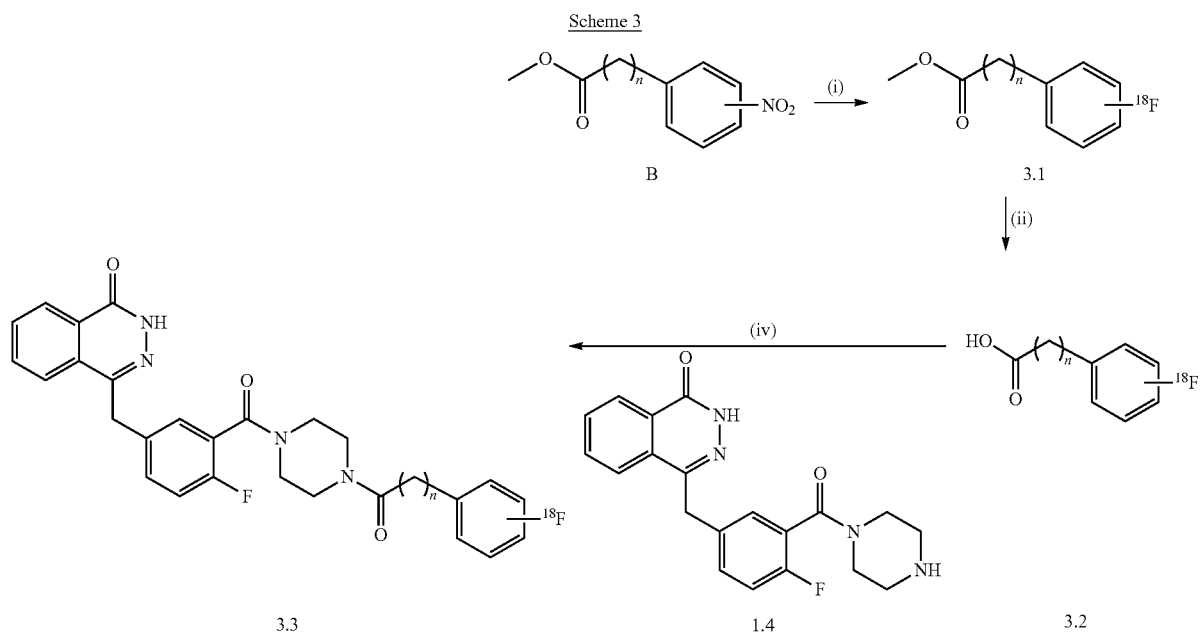

(i) K[$^{18}$F]-K$_{222}$; DMSO, 150° C., 15 min
(ii) 1) NaOH 2) HCl; DMSO, rt, 1 min
(iii) HBTU, Et$_3$N; DMSO, rt, 1 min The appropriate starting material B (m-nitro or p-nitro benzoic, phenylacetic or 3-phenylpropanoic acid ethyl ester) is added to dry K[$^{18}$F]—K$_{222}$ and heated (e.g., to 150° C. for 15 minutes for B=ethyl 4-nitrobenzoate) to give ester 3.1. Then, the ethyl protective group is removed, e.g., in the presence of sodium hydroxide, to yield add 3.2. Compound 1.4 can be synthesized according to the method described in K. A. Menear et al., "4-[3-(4 Cyclopropanecarbonylpiperazine-1-carbonyl)-4-fluorobenzyl]-2H-phthalazin-1-one: A Novel Bioavailable Inhibitor of Poly(ADP-ribose) Polymerase-1", *J. Med. Chem.* 2008, 51:6581-6591, incorporated by reference herein for the referenced synthesis. Compound 3.3 can be obtained from coupling 3.2 with 1.4 using, e.g., HBTU (N,N,N',N'-tetramethyl-O-(1H-benzotriazol-1-yl)uronium hexafluorophosphate) and Et$_3$N (triethylamine) in DMSO (dimethyl sulfoxide) at room temperature.

Uses, Formulation and Administration and Pharmaceutically Acceptable Compositions According to another embodiment, the invention provides a composition comprising a chemical entity of this invention and a pharmaceutically acceptable carrier, adjuvant, or vehicle. In certain embodiments, a composition of this invention is formulated for administration to a patient in need of such composition. In some embodiments, a composition of this invention is formulated for oral administration to a patient. In some embodiments, a composition of this invention is formulated for parenteral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the chemical entity with which it is formulated. Pharmaceutically acceptable carriers, adjuvants or vehicles that may be used in the compositions of this invention include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered parenterally. In some embodiments, the compositions are administered intrathecally or intracranially. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of chemical entities of this invention include mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Pharmaceutically acceptable compositions of this invention can also formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of chemical entities of the present invention that may be combined with the carrier materials to produce a composition in a single dosage form will vary depending upon a variety of factors, including the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific chemical entity employed, the age, body weight, general health, sex, diet, time of administration, rate of excretion, drug combination, and the judgment of the treating physician and the severity of the particular disease being treated. The amount of a chemical entity of the present invention in the composition will also depend upon the particular chemical entity in the composition.

Uses of Chemical Entities and Pharmaceutically Acceptable Compositions

As used herein, the terms "treatment", "treat" and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the chemical entities and compositions, according to the method of the present invention, can be administered using any amount and any route of administration effective for treating or lessening the severity of a disease or disorder associated with overexpression of PARP1.

In some embodiments, the chemical entities and compositions, according to the method of the present invention, can be administered using any amount and any route of administration effective for treating or lessening the severity of, e.g., one or more cancers. Such cancers include cardiac cancers, lung cancers, gastrointestinal cancers, genitourinary tract cancers, liver cancers, bone cancers, nervous system cancers, gynecological cancers, hematologic cancers, skin cancers and adrenal gland cancers.

Examples of cardiac cancers include sarcoma, e.g., angiosarcoma, fibrosarcoma, rhabdomyosarcoma, and liposarcoma; myxoma; rhabdomyoma; fibroma; lipoma and teratoma.

Examples of lung cancers include bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

Examples of gastrointestinal cancer include cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

Examples of genitourinary tract cancers include cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

Examples of liver cancers include hepatoma, e.g., hepatocellular carcinoma; cholangiocarcinoma; hepatoblastoma; angiosarcoma; hepatocellular adenoma; and hemangioma.

Examples of bone cancers include osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

Examples of nervous system cancers include cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiforme, oligodendroglioma, schwannoma, retinoblastoma, and congenital tumors; and cancers of the spinal cord, e.g., neurofibroma, meningioma, glioma, and sarcoma.

Examples of gynecological cancers include cancers of the uterus, e.g., endometrial carcinoma;

cancers of the cervix, e.g., cervical carcinoma, and pre tumor cervical dysplasia; cancers of the ovaries, e.g., ovarian carcinoma, including serous cystadenocarcinoma, epithelial cancer, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

Examples of hematologic cancers include cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia.

Examples of skin cancers include malignant melanoma, basal cell carcinoma, squamous cell carcinoma, Kaposi's sarcoma, moles dysplastic nevi, lipoma, angioma, dermatofibroma, keloids, and psoriasis.

Examples of Adrenal Gland Cancers Include Neuroblastoma.

In some embodiments, the present invention provides a method of treating cancer described herein, comprising administering a chemical entity of the invention in conjunction with one or more pharmaceutical agents. Suitable pharmaceutical agents that may be used in combination with the chemical entities of the present invention include anti-cancer agents, such as chemotherapeutic or anti-proliferative agents.

Chemotherapeutic or anti-proliferative agents include proapoptotic agents, microtubule stabilizing agents, inhibitors of mitogen-activated protein kinase signaling agents, mTOR inhibitors, TOR inhibitors, interferon agonists, matrix metalloproteinase inhibitors, proteasome inhibitors, protein A-based immune modulators, protein kinase C inhibitors, protein tyrosine phosphatase inhibitors, purine nucleoside phosphorylase inhibitors, raf antagonists, ras farnesyl protein transferase inhibitors, ras inhibitors, ribozymes, ras-GAP inhibitors, Syk inhibitors, ALL-TK antagonists, angiogenesis inhibitors, apoptosis gene modulators, apoptosis regulators, BCR/ABL antagonists, bFGF inhibitors, casein kinase inhibitors, cartilage derived inhibitors, multiple drug resistance gene inhibitors, insulin-like growth factor-1 receptor inhibitors, matrilysin inhibitors, MIF inhibitors, glutathione inhibitors, phosphatase inhibitors, plasminogen activator inhibitors, telomerase inhibitors, translation inhibitors, tyrosine kinase inhibitors, urokinase receptor antagonists, UBC inhibitors, biological response modifiers (e.g., interferon alpha, etc.), adrenocortical suppressants (e.g., mitotane, aminoglutethimide), thymopoietin receptor agonists, stromelysin inhibitors, stem cell inhibitors, stem-cell division inhibitors, Sdi 1 mimetics, signal transduction inhibitors and signal transduction modulators.

Examples of known chemotherapeutic or anti-proliferative agents include Adriamycin, dexamethasone, vincristine, cyclophosphamide, fluorouracil, topotecan, taxol, interferons (e.g., interferon alfa-2a; interferon alfa-2b; interferon alfa-n1; interferon alfa-n3; interferon beta-1a; interferon gamma-1b, etc.), interleukins (e.g., interleukin 2, including recombinant interleukin 2, also known as rIL2), platinum derivatives (e.g., lipophilic platinum agents, platinum compounds, platinum coordination complexes (e.g., cisplatin, carboblatin, etc.), platinum-triamine complexes, etc.), anti-CD20 antibodies (e.g., rituximab (Rituxan®), ocreluzimab, ofatumumab (Arzerra®), obinutuzumab (Gazyva®), Ha20 (IMMU-106, etc.)), anti-CD22 antibodies (e.g., belimumab (Benlysta®), epratuzumab, etc.), taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, purpurins, beta lactam derivatives, camptothecin derivatives, clomifene analogues, combretastatin analogues, monoclonal antibodies, oligonucleotides, lytic peptides, linear polyamine analogues, lipophilic disaccharide peptides, mismatched double stranded RNA, N-substituted benzamides, cryptophycin A derivatives, cyclopentanthraquinones, estrogen agonists, estrogen antagonists, estramustine analogues, multiple tumor suppressor 1-based therapys, imidazoacridones, immunostimulant peptides, mitomycin analogues, antisense oligonucleotides, superactive vasoactive intestinal peptide antagonists, synthetic glycosaminoglycans, thyroid stimulating hormones, alkylating agents (e.g., nitrogen mustards (e.g., mechlorethamine, cyclophosphamide, chlorambucil, melphalan, etc.), alkyl sulfonates (e.g., busulfan, etc.), nitrosoureas (e.g., carmustine, lomustine, semustine, streptozocin, etc.), erythrocyte gene therapies, antimetabolites (e.g., folic acid analogs such as methotrexate, etc.), pyrimidine analogs (e.g., fluorouracil, floxuridine, cytarabine, etc.), purine analogs (e.g., mercaptopurine, thioguanine, pentostatin, etc.), natural products (e.g., vinca alkaloids such as vinblastin, vincristine, etc.), epipodophyllotoxins (e.g., etoposide, etc.), antibiotics (e.g., daunorubicin, doxorubicin, bleomycin), enzymes (e.g., L-asparaginase, etc.), hormones (adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide)), anthracenediones (e.g., mitoxantrone, etc.), substituted ureas (e.g., hydroxyureas, etc.), methyl hydrazine derivatives (e.g., procarbazine, etc.), triazenes (decarbazine, etc.), ethylenimine and methylmelamines (e.g., hexamethylmelamine, thiotepa, etc.), thrombopoietin mimetics, baccatin III derivatives, and anti-thromboembolic agents (such as thrombolytic agents (e.g., altepase anistreplase, streptokinase, urokinase or tissue plasminogen activator, etc.), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, YM150, etc.), factor Vila inhibitors, ticlopidine, clopidogrel, CS-747 (prasugrel, LY640315), ximelagatran, BIBR1048, etc.), among others. In other embodiments, a compound of the present invention is administered in combination with a biologic agent, such as Avastin or VECTIBIX.

In some embodiments, a provided chemical entity is administered in combination with an antiproliferative or chemotherapeutic agent selected from any one or more of abarelix, acivicin, aclarubicin, acodazole hydrochloride, acronine, adozelesin, aldesleukin, alemtuzumab, alitretinoin, allopurinol, altretamine, ambomycin, ametantrone acetate, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene hydrochloride, bisnafide dimesylate, bizelesin, BCG Live, bevacuzimab, fluorouracil, bexarotene, bleomycin, bleomycin sulfate, bortezomib, brequinar sodium, bropirimine, bryostatin, busulfan, cactinomycin, calusterone, capecitabine, camptothecin, caracemide, carbetimer, carboplatin, carmustine, carubicin hydrochloride, carzelesin, cedefingol, celecoxib, cetuximab, chlorambucil, chlorofusin, cirolemycin, cisplatin, cladribine, clofarabine, crisnatol mesylate, cyclophosphamide, cytarabine, cytarabine ocfosfate, dactinomycin, darbepoetin alfa, dacarbazine, daunorubicin, daunorubicin hydrochloride, decitabine, denileukin, dexormaplatin, dexrazoxane, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin, epirubicin hydrochloride, epoetin alfa, erbulozole, esorubicin hydrochloride, erlotinib, estramustine, estramustine phosphate sodium, etanidazole, etoposide phosphate, etoposide, etoprine, exemestane, fadrozole hydrochloride, fazarabine, fenretinide, filgrastim, floxuridine, fludarabine, fludarabine phosphate, flavopiridol, floxuridine, fluorocitabine, fosquidone, fostriecin sodium, geldanamycin, gemcitabine, gemcitabine hydrochloride, genasense; gossyphol, fulvestrant, gefitinib, gemcitabine, gemtuzumab, goserelin acetate, histrelin acetate, hydroxyurea, ibritumomab, idarubicin, idarubicin hydrochloride, ifosfamide, ilmofosine, imatinib (Gleevec™), imatinib mesylate, interferon alfa-2a, interferon alfa-2b, interferon alfa-n1, interferon alfa-n3, interferon beta-1a, interferon gamma-1b, iproplatin, irinotecan, irinotecan hydrochloride, lanreotide acetate, lenalidomide, letrozole, leucovorin, leuprolide acetate, levamisole, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, 6-MP, mesna, methotrexate, methotrexate sodium, methoxsalen, metoprine, meturedepa, mitindomide, mitocarcin, mitocromin, mitogillin, mitomalcin, mitomycin, mitomycin C, mitosper, mitotane, mitoxantrone, mitoxantrone hydrochloride, mycophenolic acid, nandrolone, nelarabine, nocodazole, nofetumomab, nogalamycin, oblimersen sodium, ormaplatin, oprelvekin, oxaliplatin, oxisuran, paclitaxel (Taxol™) and analogs thereof, such as Taxotere™, palifermin, pamidronate, pegademase, pegaspargase, pegfilgrastim, peliomycin, pemetrexed disodium, pentamustine, pentostatin, peplomycin sulfate, perfosfamide, pipobroman, piposulfan, piroxantrone hydrochloride, plicamycin, plomestane, pomalidomide, porfimer sodium, porfiromycin, prednimustine, procarbazine, procarbazine hydrochloride, puromycin, puromycin hydrochloride, pyrazofurin, quinacrine, rasburicase, rituximab, riboprine, rogletimide; safingol; safingol hydrochloride; sargramostim, semustine; simtrazene; sorafenib, sparfosate sodium; sparsomycin; spirogermanium hydrochloride; spiromustine; spiroplatin; streptonigrin, streptozocin, sulofenur, sunitinib maleate, talc, talisomycin, tamoxifen, tamoxifen methiodide, tecogalan sodium, tegafur, teloxantrone hydrochloride, temoporfin, temozolomide, teniposide, teroxirone, VM-26, testolactone, thiamiprine, thioguanine, 6-TG, thiotepa, tiazofurin, tirapazamine, topotecan, toremifene, toremifene citrate, tositumomab, trastuzumab, trestolone acetate, tretinoin, triciribine phosphate, trimetrexate, trimetrexate glucuronate, triptorelin, tubulozole hydrochloride, ATRA, uracil mustard, uredepa, valrubicin, vapreotide, verteporfin, vinblastine, vinblastine sulfate, vincristine, vincristine sulfate, vindesine, vindesine sulfate, vinepidine sulfate, vinglycinate sulfate, vinleurosine sulfate, vinorelbine, vinorelbine tartrate, vinrosidine sulfate, vinzolidine, vinzolidine sulfate, vorozole, zeniplatin; zinostatin zoledronate, zoledronic acid, zorubicin and zorubicin hydrochloride.

In some embodiments, a provided chemical entity is administered in combination with an antiproliferative or chemotherapeutic agent selected from any one or more of polyphenol E, all trans-retinoic acid (ATRA), tumor necrosis factor-related apoptosis-inducing ligand (TRAIL), 5-aza-2'-deoxycytidine, all trans retinoic acid, 17-N-Allylamino-17-Demethoxygeldanamycin (17-AAG), LY294002, BAY 11-7082, PKC412, PD184352, 20-epi-1,25 dihydroxyvitamin D3, 5-ethynyluracil, abiraterone, aclarubicin, acylfulvene, adecypenol, adozelesin, ambamustine, amidox, amifostine, aminolevulinic acid, amrubicin, amsacrine, anagrelide, andrographolide, antagonist D, antagonist G, antarelix, anti-dorsalizing morphogenetic protein-1, antiandrogen, prostatic carcinoma, antiestrogen, antineoplaston, aphidicolin glycinate, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, balanol, batimastat, benzochlorins, benzoylstaurosporine, beta-alethine, betaclamycin B, betulinic acid, bicalutamide, bisantrene, bisaziridinylspermine, bisnafide, bistratene A, bizelesin, breflate, bropirimine, budotitane, buthionine sulfoximine, calcipotriol, calphostin C, canarypox IL-2, carboxamide-amino-triazole, carboxyamidotriazole, CaRest M3, CARN 700, carzelesin, castanospermine, cecropin B, cetrorelix, chlorins, chloroquinoxaline sulfonamide, cicaprost, cis-porphyrin, clotrimazole, collismycin A, collismycin B, combretastatin A4, conagenin, crambescidin 816, crisnatol, cryptophycin 8, curacin A, cycloplatam, cypemycin, cytolytic factor, cytostatin, dacliximab, decitabine, dehydrodidemnin B, deslorelin, dexifosfamide, dexverapamil, diaziquone, didemnin B, didox, diethylnorspermine, dihydro-5-azacytidine, 9-dioxamycin, diphenyl spiromustine, docosanol, dolasetron, doxifluridine, droloxifene, dronabinol, duocarmycin SA, ebselen, ecomustine, edelfosine, edrecolomab, eflornithine, elemene, emitefur, epirubicin, episteride, etanidazole, etoposide phosphate, fadrozole, fazarabine, fenretinide, finasteride, flavopiridol, flezelastine, fluasterone, fluorodaunorunicin hydrochloride, forfenimex, formestane, fostriecin, fotemustine, gadolinium texaphyrin, gallium nitrate, galocitabine, ganirelix, gelatinase inhibitors, hepsulfam, heregulin, hexamethylene bisacetamide, hypericin, ibandronic acid, idarubicin, idoxifene, idramantone, ilomastat, imiquimod, iobenguane, iododoxorubicin, 4-ipomeanol, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide+estrogen+progesterone, leuprorelin, liarozole, lissoclinamide 7, lobaplatin, lombricine, lometrexol, lonidamine, losoxantrone, lovastatin, loxoribine, lurtotecan, lutetium texaphyrin, lysofylline, maitansine, mannostatin A, marimastat, masoprocol, maspin, menogaril, merbarone, meterelin, methioninase, metoclopramide, mifepristone, miltefosine, mirimostim, mitoguazone, mitolactol, mitonafide, mitotoxin fibroblast growth factor-saporin, mofarotene, molgramostim, human chorionic gonadotrophin, monophosphoryl lipid A+*mycobacterium* cell wall sk, mopidamol, mycaperoxide B, mycobacterial cell wall extract, myriaporone, N-acetyldinaline, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, onapristone, ondansetron, ondansetron, oracin, oral cytokine inducer, ormaplatin, osaterone, oxaunomycin, palauamine, palmitoylrhizoxin, pamidronic acid, panaxytriol, panomifene, parabactin, pazelliptine, peldesine, pentosan polysulfate sodium, pentrozole, perflubron, perfosfamide, perillyl alcohol, phenazinomycin, phenylacetate, picibanil, pilocarpine hydrochloride, pirarubicin, piritrexim, placetin A, placetin B, porfimer sodium, porfiromycin, prednisone, propyl bis-acridone, prostaglandin J2, microalgal, pyrazoloacridine, pyridoxylated hemoglobin polyoxyethylerie conjugate, raltitrexed, ramosetron, retelliptine demethylated, rhenium Re 186 etidronate, rhizoxin, RII retinamide, rogletimide, rohitukine, romurtide, roquinimex, rubiginone B1, ruboxyl, safingol, saintopin, SarCNU, sarcophytol A, semustine, senescence derived inhibitor 1, sense oligonucleotides, single chain antigen-binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stipiamide, sulfinosine, suradista, suramin, swainsonine, tallimustine, tauromustine, tazarotene, tecogalan sodium, tegafur, tellurapyrylium, temoporfin, tetrachlorodecaoxide, tetrazomine, thaliblastine, thiocoraline, thrombopoietin, thymalfasin, thymotrinan, tin ethyl etiopurpurin, tirapazamine, titanocene bichloride, topsentin, toremifene, totipotent stem cell factor, triacetyluridine, triciribine, trimetrexate, triptorelin, tropisetron, turosteride, tyrphostins, ubenimex, urogenital sinus-derived growth inhibitory factor, vapreotide, variolin B, vector system, velaresol, veramine, verdins, verteporfin, vinxaltine, vitaxin, vorozole, zanoterone, zeniplatin, zilascorb and zinostatin stimalamer.

In some embodiments, a provided chemical entity is administered in combination with an antiproliferative or chemotherapeutic agent selected from any one or more of Erbulozole (also known as R-55104), Dolastatin 10 (also known as DLS-10 and NSC-376128), Mivobulin isethionate (also known as CI-980), NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armaad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B. D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbot), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Because the provided chemical entities have affinity for PARP1, any activity that induces PARP1 expression or localization of PARP1 to DNA is expected to potentiate the activity (therapeutic or diagnostic) of these compounds, and of any radiohalide-labeled PARP inhibitor. The physiological function of PARP is to repair DNA breaks; accordingly, any activity that causes DNA breaks is expected to potentiate the activity of these compounds. Because radiotherapy damages cells by causing DNA breaks, there was an expectation that PARP inhibitors would be synergistic with radiotherapy. Several studies have shown that this is, indeed, the case both in vitro and in vivo. (C. Underhill et al.& nn.59-63). Similarly, alkylating agents cause DNA damage, and continuous administration of an alkylating agent depletes MGMT, an enzyme that is necessary for repair of damage to DNA caused by alkylating agents and which can be induced by radiotherapy. Thus, synergy between (alkylating agent) temozolomide and radiotherapy has been observed in vitro, and the addition of temozolomide to radiotherapy for newly diagnosed glioblastoma resulted in a clinically meaningful and statistically significant survival benefit with minimal additional toxicity. R. Stupp et al., "Radiotherapy plus Concomitant and Adjuvant Temozolomide for Glioblastoma", *N. Engl. J. Med.* 2005, 352:987-996 & nn.31-33. See also P. Y. Wen and S. Kesari, "Malignant Gliomas in Adults", *N. Engl. J. Med.* 2008, 359:492-507.

In some embodiments, the patient in need of treatment has received or is receiving therapy that induces PARP1 expression or localization of PARP1 to DNA. In some embodiments, the patient in need of treatment has received or is receiving radiotherapy. In some embodiments, the patient in need of treatment has been or is being administered a DNA-damaging agent. In some embodiments, the DNA-damaging agent is an alkylating agent.

In some embodiments, the present invention provides the use of a chemical entity of the invention in the manufacture of a medicament for the treatment of a disease or disorder associated with overexpression of PARP1. In some embodiments, the present invention provides the use of a chemical entity of the invention in the manufacture of a medicament for the treatment of cancer. In some embodiments, the cancer is a brain malignancy. In some embodiments, the brain malignancy is glioma. In some embodiments, the brain malignancy is glioblastoma multiforme. In some embodiments, the cancer is breast cancer, ovarian cancer, endometrial cancer, lung cancer, skin cancer, or non-Hodgkin's lymphoma.

In some embodiments, the present invention provides methods for tumor imaging using PET or SPECT. A provided method comprises administering to a subject an image-generating amount of a chemical entity (including $^{18}$F-PARP1i-FL) of the invention, and measuring the distribution of the compound by PET (if labeled with $^{124}$I or $^{18}$F) or SPECT (if labeled with $^{123}$I or $^{131}$I). An image-generating amount is that amount which is at least able to provide an image in a PET or SPECT scanner, taking into account the scanner's detection sensitivity and noise level, the age of the isotope, the body size of the subject and route of administration, all such variables being exemplary of those known and accounted for by calculations and measurements known to those skilled in the art. In some embodiments, the tumor is a glioblastoma (e.g., glioblastoma multiforme) tumor, and the chemical entity is C-2a ($^{123}$I). In some embodiments, the tumor is a glioblastoma (e.g., glioblastoma multiforme) tumor, and the chemical entity is C-2b ($^{124}$I). In some embodiments, the tumor is a glioblastoma (e.g., glioblastoma multiforme) tumor, and the chemical entity is C-2d ($^{131}$I). In some embodiments, the tumor is a glioblastoma (e.g., glioblastoma multiforme) tumor, and the chemical entity is C-2f ($^{18}$F).

In some embodiments, said administering comprises administering to a subject a composition comprising an image-generating amount of a chemical entity of the invention and a pharmaceutically acceptable carrier, adjuvant, or vehicle. Such compositions may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered parenterally. In some embodiments, the compositions are administered intrathecally or intracranially.

In some embodiments, a provided chemical entity is introduced into a subject in a detectable quantity; and after sufficient time has passed for the chemical entity to become associated with tumor tissues or cells, the chemical entity is detected noninvasively inside the patient. In some embodiments, a provided chemical entity is introduced into a subject, sufficient time is allowed for the chemical entity to become associated with tumor tissues, and then a sample of tissue from the subject is removed and the chemical entity in the tissue is detected apart from the subject. In some embodiments, a tissue sample is removed from a subject and a provided chemical entity is introduced into the tissue sample. After a sufficient amount of time for the provided chemical entity to become associated with tumor tissues, the chemical entity is detected. The term "tissue" means a part of a subject's body. Examples of tissues include the brain, heart, liver, blood vessels, and arteries. A detectable quantity is a quantity of chemical entity necessary to be detected by the detection appropriate to the radiohalide. The amount of chemical entity to be introduced into a subject in order to provide for detection can readily be determined by those skilled in the art. For example, increasing amounts of the chemical entity can be given to a subject until the chemical entity is detected by the appropriate detection method.

EXAMPLES

Materials and Methods for Iodinated Compounds.
Materials.
Unless otherwise noted, all reagents were purchased from Sigma-Aldrich (St. Louis, Mo.) and used without further purification. N-succinimidyl-4-(tributylstannyl)benzoate was purchased from Synthonix (Cambridge, UK), 3-(3-iodophenyl)propionic acid and 3-(4-iodophenyl)-propionic acid from Matrix Scientific (Columbia, S.C.) and 4-iodophenyl acetic acid from Alfa Aesar (Cambridge, UK). Olaparib (AZD2281) was purchased from LC Laboratories (Woburn, Mass.). 4-(4-fluoro-3-(piperazine-1-carbonyl)benzyl)phthalazin-1(2H)-one was synthesized as described in K. A. Menear et al., "4-[3-(4 Cyclopropanecarbonylpiperazine-1-carbonyl)-4-fluorobenzyl]-2H-phthalazin-1-one: A Novel Bioavailable Inhibitor of Poly(ADP-ribose) Polymerase-1", *J. Med. Chem.* 2008, 51:6581-6591. [$^{131}$I]—NaI was purchased from Nordion (Ottawa, ON, Canada) in NaOH solution (0.1 M) with a concentration of 0.99-2.5 mCi/A. [$^{124}$I]—NaI was produced at Memorial Sloan-Kettering Cancer Center ("MSKCC", New York, N.Y.) in NaOH solution (0.5 M) with a concentration of 0.20-0.40 mCi/A.

The human glioblastoma cell lines U251 MG and U87 MG were generously provided by the Laboratory of Dr. Ronald Blasberg (MSKCC, New York, N.Y.). All cells lines were grown in Eagle's Minimal Essential Medium (MEM) containing 10% (vol/vol) heat inactivated fetal bovine serum, 100 IU penicillin, and 100 µg/mL streptomycin. Cells were cultured at 37° C. in a humidified 5% $CO_2$ atmosphere. All media was purchased from the media preparation facility at MSKCC (New York, N.Y.).

Mouse Models for Iodinated Compounds.
6-10 week old female athymic nude CrTac:NCr-Fo mice from Taconic Laboratories (Hudson, N.Y.) were used for all mouse experiments. During subcutaneous injections, mice were anesthetized using 2% isoflurane gas in 2 L/min medical air. During orthotopic injections, mice were anesthetized using a 150 mg/kg ketamine and 15 mg/kg xylazine cocktail (10 AM). Before all intravenous injections, mice were gently warmed with a heat lamp, placed in a restrainer, and tails sterilized with alcohol pads. The lateral tail vein was used for all intravenous injections.

Methods.
$^1$H NMR spectra were recorded at room temperature on a Bruker Avance 500 instrument operating at the frequency of 500 MHz (Billerica, Mass.), and internally referenced to the residual solvent peaks, $CDCl_3$ (7.26 ppm) or dimethyl sulfoxide (DMSO)-$d_6$ (2.49 ppm). Mass spectroscopy data was recorded on a Waters Acquity Ultra Performance LC (Milford, Mass.). High-resolution mass data was recorded on a Waters LCT Premier XE mass spectrometer. High-Performance Liquid Chromatography (HPLC) and Radio-HPLC were performed on a Shimadzu HPLC system equipped with 2LC-10AT pumps and an SPD-M10AVP photodiode array detector (Columbia, Md.). Radio-HPLC was performed using an identical Shimadzu system, additionally equipped with a Lablogic Scan-RAM Radio-TLC/HPLC detector (Brandon, Fla.). Analytic runs were performed on a C18 Waters Atlantis T3 column (6×250 mm, 5 mm). The solvent system included water (solvent A) and acetonitrile (AcN) (solvent B) for the purification and quality control of the radiotracers. For the purification of nonradioactive precursors, water (0.1% trifluoroacetic acid, solvent A) and acetonitrile (0.1% trifluoroacetic acid, solvent B) were used, all with a flow rate of 1 mL/min.

Materials and Methods for Fluorinated Compounds.
Materials.
Commercially available compounds were used without further purification unless otherwise stated. 4,7,13,16,21,24-Hexaoxa-1,10-diazabicyclo[8.8.8]hexacosane ($K_{222}$) was purchased from Sigma Aldrich (St. Louis, Mo.). Extra dry dimethyl sulfoxide (DMSO) over molecular sieves was purchased from Acros Organics (Geel, Belgium). Water (>18.2 MΩ·cm at 25° C.) was obtained from an Alpha-Q Ultrapure water system from Millipore (Bedford, Mass.). Olaparib (AZD2281) was purchased from LC Laboratories (Woburn, Mass.). PARP1i-FL was synthesized as described in T. Reiner et al., "Imaging Therapeutic PARP Inhibition In Vivo through Bioorthogonally Developed Companion Imaging Agents", *Neoplasia* 2012, 14:169-177. No-carrier-added (n.c.a.) [$^{18}$F]fluoride was obtained via the $^{18}$O(p,n)$^{18}$F nuclear reaction of 16.5-MeV protons in a GE Healthcare PETTrace 800 using enriched $^{18}$O-water. QMA light ion-exchange cartridges and C-18 light Sep-Pak® cartridges were obtained from Waters (Milford, Mass.).

The human glioblastoma cell lines U251 MG and U373 MG were kindly provided by the Laboratory of Dr. Ronald Blasberg (MSKCC, New York, N.Y.). Cell lines were grown in Eagle's Minimal Essential Medium (MEM), 10% (vol/vol) heat inactivated fetal bovine serum, 100 IU penicillin, and 100 µg/mL streptomycin, purchased from the culture media preparation facility at MSKCC (New York, N.Y.).

Mouse Models for Fluorinated Compounds.

Female athymic nude CrTac:NCr-Foxn1nu mice at age 6-8 weeks were purchased from Taconic Laboratories (Hudson, N.Y.). Non tumor-bearing mice were used to determine the blood half-life of C-2f ($^{18}$F) (n=3). Xenograft mouse models were used to determine the pharmacokinetics (n=12). For subcutaneous injections, mice were anesthetized with 2% isoflurane (Baxter Healthcare) (2 L/min medical air). U251 MG cells were implanted subcutaneously (5×10$^6$ cells in 150 µL 1:1 PBS/Matrigel® (BD Biosciences, San Jose, Calif.)) in the right shoulder and allowed to grow for approximately two weeks until the tumors reached 5-10 mm in diameter. For orthotopic injections, mice were anesthetized with 2% isoflurane (Baxter Healthcare) (2 L/min medical air). U251 MG cells (5×10$^5$ cells in 2 µL PBS) were injected 2 mm lateral and 1 mm anterior to the bregma using a Stoelting Digital New Standard Stereotaxic Device and a 54 Hamilton syringe. Cells were allowed to grow for approximately three weeks. For all intravenous injections, mice were gently warmed with a heat lamp and placed on a restrainer. The tails were sterilized with alcohol pads, and injection took place via the lateral tail vein.

Methods.

High performance liquid chromatography (HPLC) purification and analysis was performed on a Shimadzu UFLC HPLC system equipped with a DGU-20A degasser, an SPD-M20A UV detector, an LC-20AB pump system, and a CBM-20A communication BUS module. A LabLogic Scan-RAM radio-TLC/HPLC-detector was used for the radioactive signal. HPLC solvents (Buffer A: 0.1% TFA in water, Buffer B: 0.1% TFA in MeCN) were filtered before use. HPLC analysis and purification was performed on a reversed phase Phenomenex Gemini column (C6-Phenyl, 5 µm, 4.6 mm, 250 mm). Analysis was performed with Method A (flowrate: 1.5 mL/min; gradient: 0-14 min 5-100% B; 14-17.5 min 100% B; 17.5-18 min 100%-5% B); purification was performed with Method B (flowrate: 1.5 mL/min; isocratic: 0-14 min 5-100% B; 14-17.5 min 100% B; 17.5-18 min 100%-5% B). Electrospray ionization mass spectrometry (ESI-MS) spectra were recorded with a Shimadzu LC-2020 with electrospray ionization SQ detector. All PET imaging experiments were conducted on a microPET INVEON camera equipped with a CT scanner (Siemens, Knoxville, Tenn.). Digital phosphor autoradiography of orthotopic U251 MG tumors with surrounding brain tissue as well as muscle were obtained using a Typhoon FLA 7000 laser scanner from GE Healthcare (Port Washington, N.Y.).

Example A. Synthesis of Non-Radiolabeled ("Cold") Reference Compounds

Reference compounds c-1 to c-6 have the same structure as compounds C-1 to C-6, above, but contain the indicated isotope in place of the radiohalide.

Example A.1. Compound c-2 ($^{19}$F)

To 20 mg (54.5 µmol) of 4-(4-fluoro-3-(piperazine-1-carbonyl)benzyl)phthalazin-1(2H)-one dissolved in 1 mL of MeCN, 9.2 mg (65.5 µmol) 4-fluorobenzoic acid was added followed by 24.8 mg (65.5 µmol) of HBTU and 18 µL (131 µmol) of Et$_3$N. The reaction mixture was stirred for 5 minutes and purified by HPLC to yield the compound as an orange solid (11.5 mg, 23.5 µmol, 43%). $^1$H-NMR (500 MHz, CDCl$_3$) δ=10.74 (s, 1H), 8.51-8.49 (d, 1H), 7.83-7.76 (m, 2H), 7.82 (s, 1H), 7.45-7.44 (m, 2H), 7.38-7.36 (m, 2H), 7.14-7.08 (m, 3H), 4.33 (s, 2H), 3.75-3.39 (m, 8H). MS-ESI m/z [M+Na]$^+$=511.2. HRMS-ESI m/z calculated for [C27H22N4O3F2Na]$^+$ 511.1558, found 511.1569 [M+Na]$^+$.

Example A.2. Compound c-1 ($^{127}$I): 4-(4-fluoro-3-(4-(3-iodobenzoyl)piperazine-1-carbonyl)benzyl)-phthalazin-1(2H)-one To a solution of 4-(4-fluoro-3-(piperazine-1-carbonyl)benzyl)phthalazin-1(2H)-one (10 mg, 0.0275 mmol), triethylamine (40 µL, 0.3 mmol) and HBTU (16 mg, 0.0413 mmol) in dimethyl formamide (DMF, 500 µL) was added to 3-iodobenzoic acid (6 mg, 0.0275 mmol). The mixture was stirred at room temperature for 20 h. The crude product was then purified by preparative HPLC and dried under vacuum, yielding a white solid (6.9 mg, 48% yield). $^1$H NMR (CDCl$_3$) δ=10.00 (s, 1H), 8.40-8.38 (m, 1H), 7.71-7.69 (m, 4H), 7.64-7.63 (m, 1H), 7.30-7.26 (m, 3H), 7.09 (m, 1H), 7.04-6.87 (m, 1H), 4.21 (s, 2H), 3.71-3.29 (m, 8H). LC-ESI-MS (+) m/z=597.1 [M+H+]$^+$. HRMS-ESI [M−H+]$^-$ m/z calculated for [C$_{27}$H$_{22}$FIN$_4$O$_3$]$_-$ 595.0642, found 595.0660.

Example A.3. Compound c-2 ($^{127}$I): 4-(4-fluoro-3-(4-(4-iodobenzoyl)piperazine-1-carbonyl)benzyl)-phthalazin-1(2H)-one A solution of 4-(4-fluoro-3-(piperazine-1-carbonyl)benzyl)phthalazin-1(2H)-one (10 mg, 0.0275 mmol), HBTU (16 mg, 0.0413 mmol) triethylamine (40 µL, 0.3 mmol) and 4-iodobenzoic acid (6 mg, 0.0245 mmol) in DMF (500 µL) was stirred overnight at room temperature. The crude product was purified by preparative HPLC and dried under vacuum, yielding a white solid (8.8 mg, 61% yield). $^1$H NMR (CDCl$_3$) δ=10.48 (s, 1H), 8.40-8.39 (m, 1H), 7.74-7.66 (m, 5H), 7.27-7.26 (d, 2H), 7.09-7.07 (d, 2H), 4.22 (s, 2H), 3.73-3.14 (m, 8H). LC-ESI-MS (+) m/z=597.1 [M+H+]$^+$. HRMS-ESI [M−H+]$^-$ m/z calculated for [C$_{27}$H$_{22}$FIN$_4$O$_3$]$^-$ 595.0642, found 595.0640.

Example A.4. Compound c-3 ($^{127}$I): 4-(4-fluoro-3-(4-(2-(3-iodophenyl)acetyl)piperazine-1-carbonyl)-benzyl)phthalazin-1(2H)-one A solution of 3-iodophenyl acetic acid (6.5 mg, 0.048 mmol), 1-ethyl-3-(3-dimethylaminopropyl) carbodiimide (EDC) (10.5 mg, 0.055 mmol), N-hydroxy succinimide (NHS) and 600 µL DMF was stirred for 30 min at room temperature. Then, 4-(4-fluoro-3-(piperazine-1-carbonyl) benzyl)-phthalazin-1(2H)-one (10 mg, 0.0275 mmol) was added to the solution and the mixture was stirred at room temperature overnight. The reaction was washed with 500 µL of H$_2$O and extracted with 500 µL dichloromethane (DCM). The resulting organic solution was purified on silica gel, using a gradient elution from neat DCM to DCM/hexane 5:1 to obtain the desired product as a white solid (3 mg, 20% yield). $^1$H NMR (CDCl$_3$) δ=9.82 (s, 1H), 8.40-8.38 (m, 1H), 7.71-7.69 (m, 2H), 7.55-7.53 (m, 1H), 7.51-7.50 (m, 2H), 7.25-7.24 (m, 2H), 7.09-6.90 (m, 3H), 4.20 (s, 2H), 3.64-3.31 (m, 8H), 2.84 (s, 2H). LC-ESI-MS (+) m/z=633.1 [M+Na]$^+$. HRMS-ESI [M+H]$^+$ m/z calculated for [C$_{28}$H$_{24}$FIN$_4$O$_3$]$^+$ 611.0955, found 611.0948.

Example A.5. Compound c-4 ($^{127}$I): 4-(4-fluoro-3-(4-(2-(4-iodophenyl)acetyl)piperazine-1-carbonyl)-benzyl)phthalazin-1(2H)-one A solution of 4-iodophenyl acetic acid (6.5 mg, 0.048 mmol), EDC (10.5 mg, 0.055 mmol), NHS and 600 µL DMF was stirred for 30 min at room temperature. After this time, the 4-(4-fluoro-3-(piperazine-1-carbonyl)benzyl)phthalazin-1(2H)-one (10 mg, 0.0275 mmol) was added to the solution and the mixture was stirred at room temperature overnight. H$_2$O (500 µL) was added, the mixture extracted with DCM (2×500 µL), and the combined extracts dried under vacuum. The crude mixture was purified by silica column chromatography (100% DCM), and the product obtained as a white solid (8.8 mg, 61%). $^1$H NMR (CDCl$_3$) δ=9.82 (s, 1H), 8.40-8.38 (m, 1H), 7.83-7.81 (d, 1H), 7.77-7.75 (d, 1H), 7.70-7.69 (m, 2H), 7.63-7.56 (m, 3H), 7.00-6.89 (m, 3H), 4.20 (s, 2H), 3.63-3.11 (m, 8H), 2.84 (s, 2H). LC-ESI-MS (+) m/z=632.9 [M+Na]$^+$. HRMS-ESI [M+H]$^+$ m/z calculated for [C$_{28}$H$_{24}$FIN$_4$O$_3$]$^+$ 611.0955, found 611.0971.

Example A.6. Compound c-5 ($^{127}$I): 4-(4-fluoro-3-(4-(3-(3-iodophenyl)propanoyl)piperazine-1-carbonyl)benzyl)phthalazin-1(2H)-one A solution of 4-(4-fluoro-3-(piperazine-1-carbonyl)benzyl)phthalazin-1(2H)-one (10 mg, 0.0275 mmol), HBTU (16 mg, 0.0413 mmol) triethylamine (40 µL, 0.3 mmol) and 3-(3-iodophenyl)propionic acid (7.6 mg, 0.0275 mmol) in 400 µL of acetonitrile was stirred overnight at room temperature. The crude product was then purified by preparative HPLC and the isolated product dried at vacuum to obtain a white solid (5.1 mg, 38%). $^1$H NMR (CDCl$_3$) δ=10.33 (s, 1H), 8.41-8.39 (d, 1H), 7.71-7.63 (m, 3H), 7.51-7.45 (m, 2H), 7.27-7.25 (m, 2H), 7.12-6.92 (m, 3H), 4.22 (s, 2H), 3.65-3.12 (m, 8H), 2.88-2.83 (m, 2H), 2.59-2.48 (m, 2H). LC-ESI-MS (+) m/z=647.1 [M+Na]$^+$. HRMS-ESI [M+H]$^+$ m/z calculated for [C$_{29}$H$_{26}$FIN$_4$O$_3$]$^+$ 625.1112, found 625.1111.

Example A.7. Compound c-6 ($^{127}$I): 4-(4-fluoro-3-(4-(3-(4-iodophenyl)propanoyl)piperazine-1-carbonyl)benzyl) phthalazin-1(2H)-one 4-(4-Fluoro-3-(piperazine-1-carbonyl)benzyl)phthalazin-1(2H)-one (10 mg, 0.0275 mmol) was mixed with HBTU (16 mg, 0.0413 mmol) triethylamine (40 µL, 0.3 mmol) and 4-iodo 3 phenyl propionic acid (7.6 mg, 0.0275 mmol) in 400 µL of acetonitrile, and the solution was stirred overnight at room temperature. The crude product was then purified by preparative HPLC and the isolated product dried at vacuum to obtain a white solid (7.5 mg, 45%). $^1$H NMR (CDCl$_3$) δ=9.71 (s, 1H), 8.40-8.38 (d, 1H), 7.70-7.69 (m, 2H), 7.64-7.63 (m, 1H), 7.55-7.52 (m, 2H), 7.27-7.25 (m, 2H), 7.00-6.97 (m, 1H), 6.91-6.87 (m, 2H), 4.20 (s, 2H), 3.64-3.11 (m, 8H), 2.87-2.85 (m, 2H), 2.63-2.47 (m, 2H). LC-ESI-MS (+) m/z=647.1 [M+Na]$^+$. HRMS-ESI [M+Na]$^+$ m/z calculated for [C$_{29}$H$_{26}$FIN$_4$O$_3$Na]$^+$ 647.0931, found 647.0941.

Example B. Immunohistochemistry

PARP1 Expression in Tissues.

PARP1 antigen detection in glioblastoma xenografts and mouse brain was performed at MSKCC's Molecular Cytology Core Facility, using the Discovery XT processor (Ventana Medical Systems, Tucson, Ariz.) and detected using immunofluorescence (IF) staining. Paraffin-embedded formalin-fixed 3 µm sections were deparaffinized with EZPrep buffer, antigen retrieval was performed with CC1 buffer (both Ventana Medical Systems) and sections were blocked for 30 min with Background Buster solution (Innovex, Richmond, Calif.). Anti-PARP1 rabbit polyclonal antibody (sc-7150, 0.2 µg/mL; Santa Cruz Biotechnology, Santa, Cruz, Calif.) was incubated for 5 h, followed by 1 h incubation with biotinylated goat anti-rabbit IgG (Vector labs, PK6106) at a 1:200 dilution. Detection was performed with Streptavidin-HRP D (from DABMap Kit, Ventana Medical Systems), followed by incubation with Tyramide Alexa Fluor 594 (T20935; Invitrogen, Carlsbad, Calif.) prepared according to the manufacturer's instructions. Sections were counterstained with 4',6-diamidino-2-phenylindole (DAPI) and coverslipped with Mowiol® mounting medium (Sigma-Aldrich, St. Louis, Mo.). H&E (hematoxylin and eosin) staining was performed on adjacent sections for morphological evaluation of tissue characteristics.

Quantification of PARP1 Expression.

Protein expression was quantified on digitalized PARP1 stained sections, using at least 10 fields of view per section. Thresholding of the blue (nuclei stained with DAPI) and red fluorescent area (nuclei stained with PARP1) was performed using MetaMorph® Software (Molecular Devices, Sunnyvale, Calif.). PARP1 intensity was determined by measuring the red fluorescence intensity in the area of all nuclei and the % PARP1 positive nuclear area was calculated by dividing the PARP1 positive area by the DAPI positive area in each field of view.

Figure 1B:
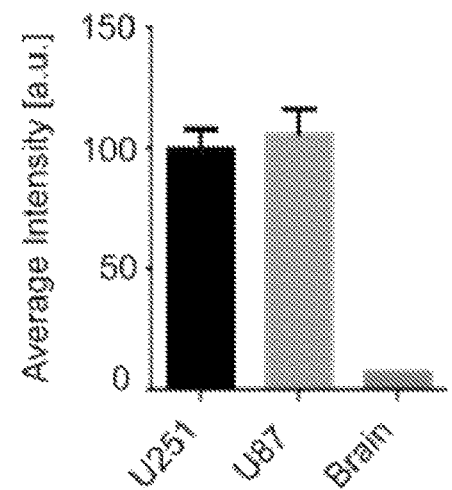
FIG. 1B illustrates the average intensity of such nuclei, determined as described in Example B.

Immunofluorescence PARP1 antigen detection in histological sections of U251 MG and U87 MG glioblastoma xenografts showed an overexpression of PARP1 compared to healthy brain tissue (image not shown). The PARP1 positive area in glioblastoma slides was increased by a factor of 15.8±8.1 (see FIG. 1A). The percent PARP1 positive area in both glioblastoma models was similar, with 42.0±10.4% and 41.5±11.0% for U251 MG and U87 MG, respectively (for healthy brain, PARP1 positive area was 2.7±1.3%). In the same way, glioblastoma tissues present similar values in average intensity (99.5±8.5 AU for U251 MG and 106.2±10.5 AU for U87 MG; see FIG. 1B) with values over 14 fold higher than healthy tissue, confirming suitable target/background ratios for in vivo evaluation.

Example 1. Synthesis of Exemplary Chemical Entities

Example 1.1. Compound C-2a ($^{123}$I)

Step 1. p-Iodobenzoic Acid Succinimide Ester (1.1.2)

To a mixture of (p-iodobenzoic acid (250 mg, 1 mmol) and EDC (300 mg, 1.5 mmol) is added dry dichloromethane (500 µL) and the mixture is stirred 30 min at 40° C. and N$_2$ atmosphere under reflux. After this time N-hydroxy succinimide (250 mg, 2.2 mmol) is added to the solution and the mixture is heated at reflux overnight under inert atmosphere. After the mixture cools, the sample is purified by chromatographic column in silica, with DCM (dichloromethane) as eluent, obtaining a white solid as product.

Step 2. N-succinimidyl-4-(tributylstannyl)benzoate (1.2.2). This Compound is Purchased from Synthonix (Cambridge, UK)

Alternatively, over a solution of 1.1.2 (25 mg, 0.072 mmol) in degassed toluene (1 mL) is added hexabutyltin (20

μL, 0.088 mmol) and tetrakis (triphenylphosphine) palladium (0) (8 mg, 0.008 mmol). The solution is heated at 150° C. in microwave for 60 minutes under nitrogen atmosphere. The sample is cooled at room temperature and solvent removed under reduced pressure. The resulting dark residue is chromatographed on silica column using dichloromethane as eluent to get the product as yellow oil.

Step 3. $^{123}$I p-Iodobenzoic Acid Succinimide Ester (1.3.2a)

Compound 1.2.2 (30 μg, 5.9 nmol) was dissolved in 30 μL of acetonitrile and added to a mixture of methanol (40 μL), Chloramine T (N-chloro tosylamide) (6 μg, 0.03 nmol) in acetic acid (2 μL) and $^{123}$I—NaI (12 μL). The reaction was kept at room temperature for 10 minutes. The mixture was then injected in the HPLC system employing a glass syringe and the product was isolated using a C18 Atlantis T3 column (4.6×250 mm, 5 μm) with the following eluents: water as solvent A and acetonitrile as solvent B, going from 5% of B to 100% of B in 15 minutes and then 100% of B from 15.01 to 25 minutes. Fraction collected with the pure compound was evaporated in vacuum.

Step 4. 4-[[4-Fluoro-3-(piperazine-1-carbonyl)phenyl]methyl]-2H-phthalazin-1-one (1.4)

This compound was synthesized according to the method described in K. A. Menear et al., "4-[3-(4 Cyclopropanecarbonylpiperazine-1-carbonyl)-4-fluorobenzyl]-2H-phthalazin-1-one: A Novel Bioavailable Inhibitor of Poly (ADP-ribose) Polymerase-1", *J. Med. Chem.* 2008, 51:6581-6591.

Step 5. 4-(4-fluoro-3-(4-(3-iodobenzoyl)piperazine-1-carbonyl)benzyl)phthalazin-1(2H)-one (1.5.2a; C-2a)

To a solution of compound 1.3.2a dispersed in 200 μL of acetonitrile was added HBTU (500 μg, 131 mmol) and 1.4.2 (500 μg, 137 mmol). The reaction was kept at 32° C. in a shaker for 3 hours at 700 rpm. The final product was isolated by HPLC employing a C18 Atlantis T3 column (4.6×250 mm, 5 μm) with the following eluents: water as solvent A and acetonitrile as solvent B, going from 5% of B to 100% of B in 15 minutes and then 100% of B from 15.01 minutes to 25 minutes. The fractions containing the radioligand were dried in vacuum, obtaining a white solid as product.

Example 1.2. Compound C-1a ($^{123}$I)

Compound C-1a can be made substantially as described for Compound C-2a, except m-iodobenzoic acid is used in place of p-iodobenzoic acid.

Example 1.3. Compound C-3a ($^{123}$I)

Compound C-3a can be made substantially as described for Compound C-2a, except 3-iodo-phenylacetic acid is used in place of p-iodobenzoic acid.

Example 1.4. Compound C-4a ($^{123}$I)

Compound C-4a can be made substantially as described for Compound C-2a, except 4-iodo-phenylacetic acid is used in place of p-iodobenzoic acid.

Example 1.5. Compound C-5a ($^{123}$I)

Compound C-5a can be made substantially as described for Compound C-2a, except 3-iodo-phenylpropionic acid is used in place of p-iodobenzoic acid.

Example 1.6. Compound C-6a ($^{123}$I)

Compound C-6a can be made substantially as described for Compound C-2a, except 4-iodo-phenylpropionic acid is used in place of p-iodobenzoic acid.

Example 1.7. Compound C-2d ($^{131}$I)

Step 1. [$^{131}$I]—N-hydroxy-succinimide benzoate

Precursor N-succinimidyl-4-(tributylstannyl)benzoate (30 μg, 5.9 nmol) was dissolved in 30 μL of acetonitrile and the solution was added to a solution of methanol (40 μL), Chloramine T (6 μg, 0.03 nmol) in acetic acid (2 μL) and $^{131}$I—NaI in NaOH 0.1 M (1-2.5 mCi). After 5 min at room temperature, the reaction was purified by HPLC using water and acetonitrile as solvents, with a gradient elution from 5% to 100% of acetonitrile over 15 min and then 100% of acetonitrile from 15 to 25 min. The retention time of $^{131}$I-N-hydroxy succinimide (NHS)-benzoate was 14.3 min and its identity was established by coelution with the reference cold compound. The radiochemical yield was 67±6% (n=12) and the radiochemical purity was >98%. The collected fraction containing $^{131}$I—NHS benzoate was concentrated to dryness under vacuum.

Step 2. Compound C-2d ($^{131}$I)

The dried radiolabeled $^{131}$I—NHS-benzoate precursor was dissolved in 200 μL of acetonitrile and an excess of HBTU (1 mg, 2.6 nmol) and 4-(4-fluoro-3-(piperazine-1-carbonyl)benzyl)phthalazin-1(2H)-one (1 mg, 2.7 nmol) was added and allowed to react for 3 h at 32° C. The final product was purified by HPLC, using water and acetonitrile as solvents with a gradient elution from 5% to 100% of solvent B over 15 min and then 100% of B from 15 to 25 min. The retention time of C-2d was 13.1 min and its identity was established by co-elution with the reference cold compound. The radiochemical yield was 72±8% (n=12) and the radiochemical purity >95%. The collected fraction containing C-2d was concentrated to dryness under reduced pressure.

Example 1.8. Compound C-2b ($^{124}$I)

Step 1. [$^{124}$I]—N-hydroxy-succinimide benzoate

[$^{124}$I]N-hydroxy-succinimide benzoate was made substantially as described for [$^{131}$I]—N-hydroxy-succinimide benzoate (Example 1.7), except [$^{124}$I]—NaI was used in place of [$^{131}$I]—NaI. The radiochemical yield was 32±5% (n=5) and the purity was >95%.

Step 2. Compound C-2b ($^{124}$I)

Compound C-2b was made substantially as described for Compound C-2d (Example 1.7), except [$^{124}$I]—NaI was used in place of [$^{131}$I]—NaI. The radiochemical yield was 68±5% (n=5) and the purity was >95%.

Example 1.9. Compound C-2f ($^{18}$F)

A QMA cartridge containing cyclotron-produced [$^{18}$F] fluoride ion was eluted with a solution containing 9 mg Kryptofix [2.2.2] (4,7,13,16,21,24-hexaoxa-1,10-diazabicyclo[8.8.8]hexacosane), 0.08 mL 0.15 M $K_2CO_3$ and 1.92 mL MeCN into a 5 mL reaction vial. Water was removed azeotropically at 120° C. 500 µg of ethyl 4-nitrobenzoate dissolved in 100 µL of DMSO was then added to the reaction vial and heated to 150° C. for 15 minutes. The reaction vial was then allowed to cool as 50 µL of 1M NaOH was added. The reaction mixture was stirred for 1 min and 50 µL of 1M HO was added to quench. Then, 2 mg of 4-(4-fluoro-3-(piperazine-1-carbonyl)benzyl)phthalazin-1(2H)-one dissolved in 1.00 µL of DMSO was added, followed by 10 mg of HBTU dissolved in 1.00 µL of DMSO and 20 µL of $Et_3N$. The reaction mixture was stirred for 1 minute. 400 µL MeCN followed by 700 µL $H_2O$ was then added and the solution was injected onto a C6-Phenyl analytical HPLC column and eluted under isocratic conditions (Method B: 30% acetonitrile in water for 35 min). Compound C-2f eluted at ($t_R$=25.5 min), which was well resolved from the nitro analogue (4-(4-fluoro-3-(4-(4-nitrobenzoyl)piperazine-1-carbonyl)benzyl)phthalazin-1(21-1)-one; tR=30.1 min). For intravenous administration, the product-containing fraction was passed through a C18 light-SepPak® cartridge preconditioned with EtOH (10 mL) and water (10 mL). The cartridge was washed with water (3 mL) and C-2f was eluted using EtOH (400 µL). The solution was then diluted with 0.9% saline to 10% EtOH. The radiochemical purity of the final formulation was confirmed using analytical HPLC. Coelution with nonradioactive c-2 ($^{19}F$) reference compound confirmed the identity of the radiotracer. To measure radiochemical and chemical purity (>99%), C-2f was reinjected onto an analytical C6-Phenyl column (gradient A: 5400% acetonitrile in water over 14 min, then 100% acetonitrile for minutes 14-18; $t_R$=11.4 min).

Example 1.10. Compound $^{18}F$-PARP1i-FL(2)

The [$^{18}F$]fluoride in water is transferred into a sealed conical drying vessel containing tetrabutylammonium bicarbonate (TBAB) (75 mM in water, 804, 1.8 mg, 6.0 µmol). Water is removed from the [$^{18}F$]F$^-$/TBAB solution by azeotropic distillation with dry acetonitrile (3×1 mL) under a gentle stream of nitrogen at 110° C. The dry residue is reconstituted with 100 µL of MeCN and cooled to room temperature. To this, PARP1i-FL (50 µg, 0.78 µmol) in MeCN (50 µL) is added, followed by 10 equivalents of $SnCl_4$ (100 mM in acetonitrile, 7.8 µmol). The mixture is then heated at 35° C. for 30 min. After incubation, the reaction mixture is cooled to room temperature and diluted with ultrapure water to reach a final 20% MeCN concentration. The crude mixture is filtered with PES 0.22 µm 30 mm diameter (Shirley, Mass.) and automatically injected into the HPLC system (gradient A) for purification. The [$^{18}F$]PARP1i-FL(2) peak is collected (rt: 17.5 min) and the solution passed through a C18 light-SepPak® cartridge (preconditioned with EtOH (5 mL) and water (5 mL). The cartridge is washed with water (3 mL) and [$^{18}F$]PARP1i-FL is eluted using EtOH (1 mL). The organic solvent is removed by rotary evaporation at 40° C., and the residual product can be formulated in 15% PEG300 in 0.9% saline for in vivo animal imaging and biodistribution.

Example 2. Biophysical Properties

Example 2.1. $IC_{50}$ Determination

Inhibition of PARP1 was measured using the Universal PARP Colorimetric Assay Kit (Trevigen®, Gaithersburg, Md.). $IC_{50}$ values were calculated using Prism 6.0c software (GraphPad, La Jolla, Calif.).

Dilutions of c-1 to c-6 ($^{127}I$) (final concentrations ranging from 3.3 µM to 0.1 nM) and c-2 ($^{19}F$) (final concentrations ranging from 1 µM to 33 µM) were incubated with 0.5 U of PARP1 high specific activity (HSA) enzyme for 10 min in histone-coated 96-well plates. All experiments were carried out in triplicate. Positive control samples did not contain inhibitor, and negative control samples did not contain PARP1. All reaction mixtures were adjusted to a final volume of 504, and a final concentration of 1% (for iodinated compounds) or 2% (for c-2 ($^{19}F$) dimethyl sulfoxide (DMSO) in assay buffer. The remainder of the assay was performed according to the manufacturer's instructions. PARP1 activity was measured by absorbance at 450 nm in each well using a SpectraMax M5 spectrophotometer with SoftMax Pro software (Molecular Devices, Sunnyvale, Calif.).

Example 2.2. Chromatographic Hydrophobicity Index (CHI) Determination

Chromatographic Hydrophobicity Index (CHI) was determined according to the procedures reported in K. Valko et al, "Chromatographic Hydrophobicity Index by Fast-Gradient RP-HPLC: A High-Throughput Alternative to log P/log D", Anal. Chem. 1997, 69:2022-29, incorporated by reference herein in its entirety. Briefly, a series of standards with known CHIs were analyzed with reverse phase HPLC. Retention times of the standards along with their known CHIs were plotted with Prism 6.0c software (GraphPad, La Jolla, Calif.). A line was fit to the data to create a calibration curve, which was then used to calculate the CHI of the test chemical entity based on the HPLC retention time.

Example 2.3. log $P_{CHI}$ Determination

The log $P_{CHI}$ value was determined according to K. Valko, 1997.

Example 2.4. Plasma Protein Binding Determination

The plasma protein fraction was determined using the Rapid Equilibrium Dialysis Device System (LifeTechnologies, Grand Island, N.Y.) according to the manufacturer's protocol.

Example 2.4.1. Plasma Protein Binding Determination of Compounds c-1 ($^{127}I$) to c-6 ($^{127}I$)

For each of the iodinated compounds, membrane dialysis was performed with 10 µM of the compound in mouse serum (500 µL) on one side of the membrane and PBS (750 µL) on the other side. The system was sealed with parafilm and incubated for 4 h at 37° C. on an orbital shaker set to 250 rpm. Thereafter, 400 µL of solution was taken from both sides, and samples were treated twice with an equal amount of AcN and vortexed to remove protein before HPLC analysis. After injection (100 µL), the compound peaks from each sample were then integrated, and the protein bound fraction was determined as % bound=[1−(Concentration buffer chamber/Concentration plasma chamber)]×100. The data was analyzed using Prism 6.0c (GraphPad Software, La Jolla, Calif.).

Example 2.4.2. Plasma Protein Binding Determination of Compound c-2 ($^{19}F$)

Membrane dialysis was performed with 500 µM c-2 ($^{19}F$) mouse serum (500 µL) on one side of the membrane and PBS (700 μL) on the other side. The system was sealed with parafilm and incubated for 4 h at 37° C. on an orbital shaker set to 100 rpm. Thereafter, 50 μL of solution was taken from both sides, and samples were treated with 300 μL of precipitation buffer (90/10 acetonitrile/water with 0.1% formic acid) and vortexed to remove protein before HPLC analysis. After injection the c-2 ($^{19}$F) peaks from each sample were integrated, and the protein bound fraction was determined as % bound=[1−(Concentration buffer chamber/Concentration plasma chamber)]×100. The data was analyzed using Prism 6.0c (GraphPad Software, La Jolla, Calif.).

Example 2.5. Octanol-Water Partition Coefficient (log $P_{O/W}$) Determination

The lipophilicity of C-2f ($^{18}$F) was determined by adding 2.5 μCi to a mixture of 0.5 mL of 1-octanol and 0.5 mL of 25 mM phosphate buffered saline (pH 7.4) and mixed for 5 minutes. Then, the mixture was centrifuged at 15000 rpm for 5 minutes. 1004 samples were obtained from organic and aqueous layers, and the radioactivity of the samples were measured in a γ-counter WIZARD$^2$ automatic γ-counter (PerkinElmer, Boston, Mass.). The experiment was performed in triplicate, and the resulting log $P_{O/W}$ was calculated as the mean±SD.

Example 3. Cell-Based and In Vivo Pharmacokinetics of Exemplary Chemical Entities Example 3.1. Blood Half-Life (In Vivo) and Stability in Whole Blood (In Vitro)

Example 3.1.1. Blood Half-Life of C-2d ($^{131}$I)

The blood half-life was determined by measuring the activity in serial blood samplings. Healthy female nude mice (8-10 weeks old, 20-25 g in weight, n=3) were injected via the tail vein with 50 μCi C-2d ($^{131}$I) in 200 μL of solution PBS/PEG$_{300}$ (10:1). Blood was sampled from the saphenous vein at 5, 15, 30, 60, 120 and 240 min post injection. Blood was weighed and radioactivity was measured on a Wizard 2470 Automatic Gamma Counter (Perkin Elmer, Waltham, Mass.). Measurements in counts per minute were calculated as the mean % ID/g. The blood half-life was calculated using Prism 6.0c (GraphPad Software, La Jolla, Calif.).

Example 3.1.2. Blood Half-Life of C-2f ($^{18}$F)

The blood half-life was calculated by measuring the activity of blood samples collected at different time points p.i. (5, 15, 30, 45, 60, 90 and 120 minutes). Female nude mice (n=3) were injected via lateral tail vein with C-2f (50 μCi in 200 μL 10% EtOH in 0.9% sterile saline) and blood samples were collected from the great saphenous vein of each animal at the predetermined time point. The collected blood was weighed and counted in a WIZARD$^2$ automatic γ-counter (PerkinElmer, Boston, Mass.). The blood half-life was calculated using Prism 6.0c (GraphPad Software, La Jolla, Calif.) using a two-phase decay least squares fitting method and expressed as % ID/g.

Example 3.1.3. Stability in Whole Blood of C-2d ($^{131}$I)

The in vitro stability was assessed by incubating 6 μCi C-2d ($^{131}$I) in mouse blood for 0 to 60 min at 37° C. At baseline, 15, 30 and 60 min, the samples were immediately placed on ice and mixed 1:1 with a solution of AcN/DMSO (250 μL) and then vigorously vortexed for 30 sec to precipitate out serum protein. The sample was centrifuged at 3000 RCF for 3 min at 4° C., and the supernatant collected. This procedure was repeated three times, and the combined supernatants analyzed by HPLC equipped with radioactive detector (Shimadzu, Kyoto, Japan), collecting samples every 30 sec. Radioactivity of each fraction was measured on a Wizard 2470 Automatic Gamma Counter (Perkin Elmer, Waltham, Mass.) and the blood stability was analyzed using Prism 6.0c (GraphPad Software, La Jolla, Calif.). The HPLC chromatograms showed only one peak at 13 min corresponding to the pure compound C-2d. The absence of other peaks, which would indicate secondary metabolites, confirmed the stability of the compound over the course of 60 min.

Example 3.1.4. Stability in Whole Blood of C-2f ($^{18}$F)

Compound C-2f ($^{18}$F) (approximately 200 μCi, 45 mCi/μmol in 200 μL, 10% EtOH in 0.9% sterile saline) was added to 250 μL of whole human blood and incubated at 37° C. for increasing lengths of time (15, 30, 60, 120 and 240 minutes). C-2f was then extracted with 750 μL of MeCN, then centrifuged (5 minutes at 5000 rpm) to pellet blood cells and proteins. The supernatant was collected and prepared for HPLC injection by adding 750 μL mQ H$_2$O and filtering. The blood stability was measured by HPLC analysis (Method A). Over the measured time period, no radioactive metabolites were observed, confirming the stability of the compound over the measured time period.

Example 3.2. Competition Assays

Example 3.2.1. In Vitro Blocking Study of Compounds c-1 ($^{127}$I) to c-6 ($^{127}$I)

Figure 2:
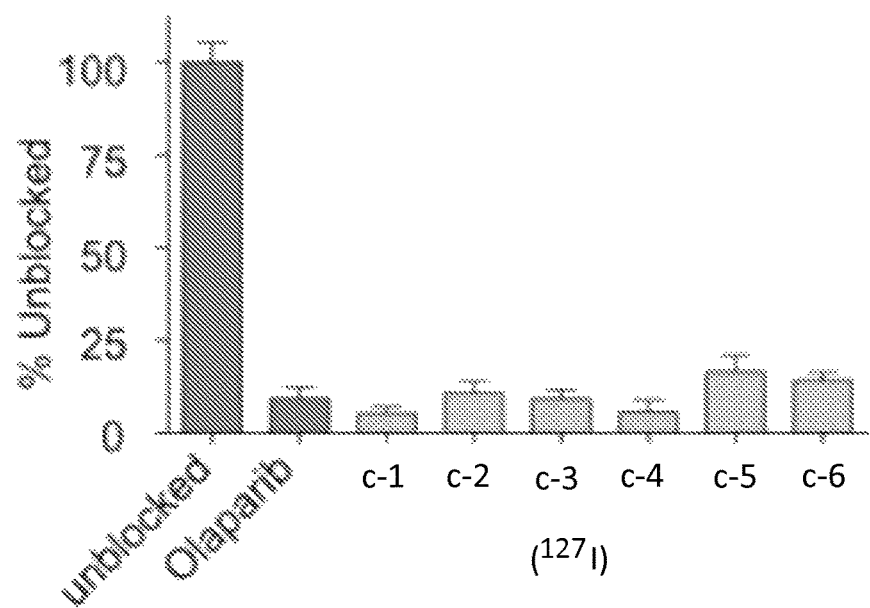
FIG. 2 illustrates the reduction in fluorescence intensity attributable to the competitive inhibition of PARP1-iFL uptake in U87 MG cells by compounds c-1 ($^{127}$I) to c-6 ($^{127}$I), determined as described in Example 3.2.1.

U87 MG cells were seeded into a 96 well plate in a concentration of 1×10$^4$ cells per well. After 24 h, the cells were incubated with either the fluorescent PARP1 inhibitor PARP1i-FL (250 nM) alone or with one of the compounds c-1 ($^{127}$I) to c-6 ($^{127}$I) at a 100-fold higher concentration (25 μM) for 20 min. Additionally, as a positive control, the PARP1 inhibitor olaparib was used. All incubation solutions also included Hoechst 33342 nuclear stain (Sigma-Aldrich, St. Louis, Mo.). The cells were washed twice with media and once with PBS for 5 min each and imaged on an LSM 5Live confocal microscope (Zeiss, Oberkochen, Germany). All wells were imaged with the DAPI filter for the Hoechst staining and the FITC filter for the PARP1i-FL staining. The DAPI and FITC channels were co-registered and the green fluorescence in the location of the Hoechst staining was quantified for each image (confocal images not shown). The percent reduction in PARP1i-FL uptake was calculated based on the level of fluorescence intensity seen in each image and normalized to the cells not receiving any of compounds c-1 to c-6 (see FIG. 2). Experiments were performed in triplicate.

Example 3.2.2. In Vitro Blocking Study of Compound c-2 ($^{19}$F)

U251 MG or U373 MG (1×10$^4$ cells per well) cells were seeded into 12 wells each on a 96-well plate and cultured for 24 hours. The cells were then incubated either alone (3×), with PARP1i-FL (500 nM) (3×), or with PARP1i-FL (500 nM) and olaparib or c-2 ($^{19}$F) in 10-fold excess (5 µM) (3× ea.) at 37° C. for 30 minutes. Following incubation, cells were washed twice with media and twice with PBS and imaged with a Zeiss LSM 5Live confocal microscope (images not shown). Fluorescence intensity was then quantified from the images using ImageJ 1.47 u processing software (see FIG. 3).

Example 3.2.3. In Vivo Blocking Study of Compound c-2 ($^{127}$I)

Nude mice bearing subcutaneous U87 MG tumors were injected with either the fluorescent PARP1 inhibitor PARP1i-FL (2.5 mg/kg, 200 µL of 19.5% 1:1 DMAC: Kolliphor, 3.5% DMSO, 77% PBS) alone, PARP1i-FL 30 min after a pre-injection of a 50-fold excess of c-2 ($^{127}$I) (125 mg/kg, 100 µL of 10% PEG$_{300}$, 90% PBS), or injected with saline alone. One hour post injection, the mice were sacrificed and the tumors were resected and imaged with the IVIS spectrum fluorescence imaging system (PerkinElmer, Waltham, Mass.) using Living Image 4.4 software (images not shown). The fluorescence intensity of the tissues is shown in FIG. 4. The tumors were also imaged microscopically with the 5Live fluorescent confocal microscope using the 488 nm laser for PARP1i-FL excitation (images not shown).

Example 3.3. Biodistribution Studies

Example 3.3.1. Biodistribution of C-2d ($^{131}$I)

Biodistribution experiments were conducted on female nude mice (8-10 weeks old and 20-25 g in weight, n=21) bearing U87 MG subcutaneous xenografts. The radiolabeled preparation (20-30 µCi of compound C-2d ($^{131}$I) in 200 µL of a solution 90% PBS 10% PEG$_{300}$) was administrated via the lateral tail vein. To determine a suitable specific activity (to achieve a sufficiently high tumor to organ ratio), several specific activities were tested (5 mCi/µmol, 50 mCi/µmol, 250 mCi/µmol) in mice bearing U87 MG tumors. The compound was allowed to circulate for 2 h post injection at which time mice were sacrificed and organs were harvested (n=3). The radioactive content in tissue of interest (blood, tumor, muscle, bone, liver, spleen, kidney, heart, lung, pancreas, brain, skin, small intestine, large intestine, stomach, tail, thyroid and feces) was measured on a Wizard 2470 Automatic Gamma Counter, and the tissue-associated activity was calculated as the mean % ID/g using the following formula: [(activity in the target organ/grams of tissue)/ injected dose]×100%. Results are shown in Tables B1, B2 and B3, below. As can be seen, administration of C-2d with a specific activity of 50 mCi/µmol showed the most favorable tumor/muscle and tumor/brain ratios of the three activities tested.

TABLE B1

| C-2d ($^{131}$I) in U87 MG | | |
| --- | --- | --- |
| Organ | 5 mCi/µmol (% ID/g) | 5 mCi/µmol (S.D.) |
| Blood | 5.88 | 4.76 |
| Tumor | 0.32 | 0.14 |
| Muscle | 0.27 | 0.30 |
| Bone | 0.14 | 0.08 |
| Liver | 3.14 | 0.64 |
| Spleen | 0.60 | 0.28 |
| Kidneys | 1.08 | 0.49 |

TABLE B1-continued

| C-2d ($^{131}$I) in U87 MG | | |
| --- | --- | --- |
| Organ | 5 mCi/µmol (% ID/g) | 5 mCi/µmol (S.D.) |
| Heart | 0.26 | 0.10 |
| Lung | 0.55 | 0.14 |
| Pancreas | 0.67 | 0.33 |
| Brain | 0.02 | 0.004 |
| Skin | 0.26 | 0.11 |
| Small intestine | 14.16 | 10.60 |
| Large intestine | 5.43 | 5.30 |
| Stomach | 5.86 | 2.76 |
| Tail | 2.31 | 1.95 |
| Thyroid | 0.37 | 0.13 |
| Feces | 6.23 | 2.90 |

TABLE B2

| C-2d ($^{131}$I) in U87 MG | | |
| --- | --- | --- |
| Organ | 50 mCi/µmol (% ID/g) | 50 mCi/µmol (S.D.) |
| Blood | 0.90 | 0.65 |
| Tumor | 0.17 | 0.06 |
| Muscle | 0.04 | 0.020 |
| Bone | 0.04 | 0.004 |
| Liver | 1.02 | 0.39 |
| Spleen | 0.15 | 0.08 |
| Kidneys | 0.35 | 0.10 |
| Heart | 0.10 | 0.02 |
| Lung | 0.28 | 0.30 |
| Pancreas | 0.42 | 0.31 |
| Brain | 0.007 | 0.002 |
| Skin | 0.092 | 0.06 |
| Small intestine | 7.17 | 5.45 |
| Large intestine | 0.94 | 0.66 |
| Stomach | 1.90 | 0.97 |
| Tail | 0.45 | 0.14 |
| Thyroid | 0.14 | 0.02 |
| Feces | 3.75 | 2.04 |

TABLE B3

| C-2d ($^{131}$I) in U87 MG | | |
| --- | --- | --- |
| Organ | 250 mCi/µmol (% ID/g) | 250 mCi/µmol (S.D.) |
| Blood | 4.78 | 2.36 |
| Tumor | 0.18 | 0.03 |
| Muscle | 0.074 | 0.03 |
| Bone | 0.09 | 0.06 |
| Liver | 2.17 | 0.19 |
| Spleen | 0.43 | 0.04 |
| Kidneys | 0.58 | 0.06 |
| Heart | 0.16 | 0.06 |
| Lung | 0.43 | 0.18 |
| Pancreas | 0.27 | 0.10 |
| Brain | 0.06 | 0.08 |
| Skin | 0.14 | 0.03 |
| Small intestine | 7.55 | 3.25 |
| Large intestine | 17.29 | 2.35 |
| Stomach | 1.25 | 0.68 |
| Tail | 0.58 | 0.28 |
| Thyroid | 0.20 | 0.05 |
| Feces | 67.25 | 24.16 |

After determining the optimal specific activity (of the three tested), a suitable time window for imaging was determined by testing the compound distribution in nude mice bearing U87 MG tumors at different time points. The compound was allowed to circulate for various times (1, 2, and 6 h), after which the mice were sacrificed (n=3). As shown in Tables B4, B5 and B6, the most favorable tumor/ muscle and tumor/brain ratios of the three time points tested were seen at 2 h post intravenous injection.

TABLE B4

C-2d ($^{131}$I) in U87 MG

| Organ | 1 h (% ID/g) | 1 h (S.D.) |
|---|---|---|
| Blood | 2.76 | 3.19 |
| Tumor | 0.50 | 0.09 |
| Muscle | 0.27 | 0.10 |
| Bone | 0.19 | 0.02 |
| Liver | 4.61 | 0.22 |
| Spleen | 0.64 | 0.24 |
| Kidneys | 1.60 | 0.13 |
| Heart | 0.39 | 0.04 |
| Lung | 0.71 | 0.08 |
| Pancreas | 0.74 | 0.09 |
| Brain | 0.034 | 0.005 |
| Skin | 0.46 | 0.06 |
| Small intestine | 13.70 | 2.47 |
| Large intestine | 1.49 | 0.08 |
| Stomach | 1.88 | 0.70 |
| Tail | 1.00 | 0.09 |
| Thyroid | 0.56 | 0.08 |
| Feces | 7.31 | 2.80 |

TABLE B5

C-2d ($^{131}$I) in U87 MG

| Organ | 2 h (% ID/g) | 2 h (S.D.) |
|---|---|---|
| Blood | 0.90 | 0.65 |
| Tumor | 0.17 | 0.06 |
| Muscle | 0.039 | 0.020 |
| Bone | 0.044 | 0.005 |
| Liver | 1.02 | 0.39 |
| Spleen | 0.15 | 0.08 |
| Kidneys | 0.35 | 0.10 |
| Heart | 0.10 | 0.02 |
| Lung | 0.28 | 0.19 |
| Pancreas | 0.42 | 0.31 |
| Brain | 0.007 | 0.002 |
| Skin | 0.091 | 0.061 |
| Small intestine | 7.16 | 5.45 |
| Large intestine | 0.94 | 0.66 |
| Stomach | 1.90 | 0.97 |
| Tail | 0.45 | 0.14 |
| Thyroid | 0.14 | 0.03 |
| Feces | 3.75 | 2.05 |

TABLE B6

C-2d ($^{131}$I) in U87 MG

| Organ | 6 h (% ID/g) | 6 h (S.D.) |
|---|---|---|
| Blood | 0.34 | 0.26 |
| Tumor | 0.13 | 0.05 |
| Muscle | 0.023 | 0.012 |
| Bone | 0.035 | 0.017 |
| Liver | 0.65 | 0.10 |
| Spleen | 0.060 | 0.005 |
| Kidneys | 0.24 | 0.08 |
| Heart | 0.075 | 0.003 |
| Lung | 0.12 | 0.03 |
| Pancreas | 0.084 | 0.033 |
| Brain | 0.008 | 0.001 |
| Skin | 0.072 | 0.002 |
| Small intestine | 1.13 | 0.17 |
| Large intestine | 1.33 | 0.12 |
| Stomach | 0.81 | 0.09 |

TABLE B6-continued

C-2d ($^{131}$I) in U87 MG

| Organ | 6 h (% ID/g) | 6 h (S.D.) |
|---|---|---|
| Tail | 0.31 | 0.06 |
| Thyroid | 0.098 | 0.002 |
| Feces | 70.67 | 7.38 |

Biodistribution studies were conducted on female nude mice (8-10 weeks old and 20-25 g in weight, n=21) bearing U251 MG subcutaneous xenografts. The radiolabeled preparation (20-30 µCi of compound C-2d ($^{131}$I) in 200 µL of a solution 90% PBS 10% PEG$_{300}$) was administered via the lateral tail vein. The compound was allowed to circulate for 2 h post injection at which time mice were sacrificed and organs were harvested (n=3). The radioactive content in tissue of interest (blood, tumor, muscle, bone, liver, spleen, kidney, heart, lung, pancreas, brain, skin, small intestine, large intestine, stomach, tail, thyroid and feces) was measured on a Wizard 2470 Automatic Gamma Counter, and the tissue-associated activity was calculated as the mean % ID/g using the following formula: [(activity in the target organ/grams of tissue)/injected dose]×100%. Results are shown in Table B7, below.

TABLE B7

C-2d ($^{131}$I) in U251 MG

| Organ | % ID/g | S.D. |
|---|---|---|
| Blood | 0.27 | 0.06 |
| Tumor | 0.43 | 0.06 |
| Muscle | 0.03 | 0.01 |
| Bone | 0.07 | 0.04 |
| Liver | 2.34 | 0.57 |
| Spleen | 0.40 | 0.10 |
| Kidneys | 0.61 | 0.17 |
| Heart | 0.16 | 0.06 |
| Lung | 0.28 | 0.12 |
| Pancreas | 0.15 | 0.05 |
| Brain | 0.01 | 0.00 |
| Skin | 0.25 | 0.09 |
| Small intestine | 11.70 | 11.40 |
| Large intestine | 1.26 | 1.15 |
| Stomach | 0.88 | 0.47 |
| Tail | 0.60 | 0.35 |
| Thyroid | 0.24 | 0.06 |
| Feces | 4.34 | 1.22 |

Example 3.3.2. Biodistribution of C-2f ($^{18}$F)

Biodistribution studies were performed in subcutaneous U251 MG xenograft bearing athymic nude mice (n=12). Mice were divided in two groups (blocked and unblocked) and administered with C-2f (approximately 50 µCi, 45 mCi/µmol in 2004, 10% EtOH in 0.9% sterile saline) via tail vein injection. The blocked group was pre-injected 30 min prior with a 500-fold excess of olaparib (18 mM, 2 µmol, in 100 µL 15% PEG$_{300}$/85% 0.9% saline). Mice were sacrificed by CO$_2$ asphyxiation at 120 min post injection and major organs were collected, weighed, and counted in a WIZARD$^2$ automatic γ-counter (PerkinElmer, Boston, Mass.). The radiopharmaceutical uptake was expressed as a percentage of injected dose per gram (% ID/g) using the following formula: [(activity in the target organ/grams of tissue)/injected dose]×100%. Results are shown in Tables B8 and B9, below. Biodistribution data was corroborated by PET/CT imaging, with whole axial and coronal slices of subcutaneous tumor-bearing mice receiving only C-2f and both olaparib/C-2f (images not shown).

TABLE B8

C-2f ($^{18}$F) in U251 MG ("unblocked")

| Organ | % ID/g | S.D. |
|---|---|---|
| Blood | 0.41 | 0.09 |
| Tumor | 1.82 | 0.21 |
| Muscle | 0.37 | 0.09 |
| Bone | 1.21 | 0.24 |
| Liver | 3.98 | 0.56 |
| Spleen | 4.04 | 1.23 |
| Kidney | 1.17 | 0.46 |
| Heart | 0.30 | 0.08 |
| Lung | 0.44 | 0.11 |
| Pancreas | 1.71 | 0.41 |
| Brain | 0.04 | 0.01 |
| Small intestine | 2.94 | 0.91 |
| Large intestine | 2.24 | 0.59 |
| Stomach | 0.73 | 0.3 |
| Lymph nodes | 2.80 | 0.51 |

TABLE B9 olaparib/C-2f ($^{18}$F) in U251 MG ("blocked")

| Organ | % ID/g | S.D. |
|---|---|---|
| Blood | 0.45 | 0.36 |
| Tumor | 0.23 | 0.09 |
| Muscle | 0.19 | 0.08 |
| Bone | 0.21 | 0.1 |
| Liver | 3.61 | 2.04 |
| Spleen | 0.26 | 0.09 |
| Kidney | 0.47 | 0.22 |
| Heart | 0.12 | 0.03 |
| Lung | 0.38 | 0.07 |
| Pancreas | 0.48 | 0.25 |
| Brain | 0.04 | 0.03 |
| Small intestine | 2.35 | 0.7 |
| Large intestine | 1.73 | 0.8 |
| Stomach | 1.05 | 0.58 |
| Lymph nodes | 0.13 | 0.03 |

Example 4. In Vivo Imaging and Autoradiography

Example 4.1. In Vivo Imaging

Example 4.1.1. SPECT/CT Imaging Using C-2d ($^{131}$I)

SPECT/CT was acquired in athymic nude mice (6-10 weeks old) bearing orthotopic U251 MG xenografts. Before administration of the radioiodinated tracer, in terms to block the thyroid, the animals were treated with an intraperitoneal injection of NaI (100₁, 0.6 mM) 60 min previous to the injection of 450-600 µCi (145-210 mCi/µmol) compound C-2d ($^{131}$I) in 200 µL PBS solution (10% PEG$_{300}$) via the lateral tail vein and then anesthetized with isoflurane mixed with medical air (2% for induction and maintenance). Animals were placed in prone position and scans were then performed at 90 min after injection during 60 min using a SPECT/CT small animal imaging system (NanoSPECT/CT, Mediso, Boston, Mass.). SPECT Images (not shown) were reconstructed using HiSPECT software and in vivo Scope software was used for CT image reconstruction.

Example 4.1.2. PET/CT Imaging Using C-2b ($^{124}$I)

PET/CT was acquired in athymic nude mice (6-10 weeks old) bearing orthotopic U251 MG xenografts. Images were acquired after the injection of 200-250 µCi (110-170 mCi/µmol) compound C-2b ($^{124}$I) in 200 µL PBS solution (10% PEG$_{300}$) via the lateral tail vein under isoflurane anaesthesia (2% for induction and 1.5% for maintenance). Mice were also treated with an intraperitoneal injection of NaI (100₁, 0.6 mM), 60 min previous to the administration of the radioiodinated tracer. Animals were immediately placed in prone position under isoflurane anesthesia and scans were then performed at 90 min after injection during 30 min using the Inveon PET/CT imaging system (Siemens, Knoxville, Tenn.). PET and CT Images (not shown) were reconstructed using Inveon research workplace software.

Example 4.1.3. PET/CT Imaging Using C-2f ($^{18}$F)

Mice bearing orthotopic U251 MG (n=8) were divided in two groups (unblocked and blocked) and administered with C-2f (150 µCi, 45 mCi/µmol in 300 µL 10% EtOH in 0.9% sterile saline) via tail vein injection. The blocked cohort (n=4) was pre-injected with olaparib (500 mM, 3.7 µmol, in 100 µL 15% PEG300/85% 0.9% saline) 30 min prior to injection of C-2f. Approximately 5 min prior to PET acquisition, mice were anesthetized by inhalation of a mixture of isoflurane (Baxter Healthcare, Deerfield, Ill., USA; 2% isoflurane, 2 L/min medical air) and positioned on the scanner bed. Anesthesia was maintained using a 1% isoflurane/O$_2$ mixture. PET data for each mouse was recorded using static scans of 10 minutes and acquired at 30 and 120 minutes post injection. Quantification (see FIG. 8) and % ID/g values were calculated by manually drawing regions of interests in three different frames and determining the average values using ASI Pro VM™ MicroPET Analysis software (Siemens Medical Solutions, Knoxville, Tex.). Images are shown in FIGS. 7A and 7B.

Example 4.1.4. PET/MRI Imaging Using C-2f ($^{18}$F)

PET images (see were acquired on integrated in-line preclinical whole-body 1 T PET/MRI system (Mediso, Budapest, Hungary). The mice of Example 4.1.3 were injected with 200 µCi of C-2f and a 20 minutes static PET scan was acquired 2 hours post injection. 200 µL of diluted gadopentate dimegumine in saline solution (1:5) (Magnevist®; Bayer Pharma, Wayne, N.J.) was administered intravenously one minute prior to MRI acquisition. Tumor regions were identified on anatomic images acquired using a post-contrast T$_1$-weighted spin-echo (SE) acquisition (T$_E$/T$_R$=12.4/671 ms, 0.3125×0.3125 mm in plane resolution and 1 mm slice thickness). 30 slices were acquired in order to cover the mouse. Data analysis and PET/MRI co-registration was performed using VivoQuant™ software (inviCro LLC, Boston, Mass.). Images are shown in FIGS. 9A-9F.

Example 4.2. Autoradiography

Example 4.2.1. Autoradiography Using C-2d ($^{131}$I)

U251 MG glioblastoma cells (5×10$^4$ in 2 µL of PBS) were orthotopically implanted in athymic nude mice, using a stereotaxic device, and the tumors allowed to grow for approximately 4 weeks. Once tumors reached sufficient size, the orthotopic U251 MG tumor-bearing mice were injected intravenously with 500 µCi compound C-2d ($^{131}$I) (in 200 µL of a solution PBS 90% PEG$_{300}$ 10%, n=2) alone or with a pre-injection of 15 µmol olaparib (in 100 µL of 7.5% DMSO, 12.5% PEG$_{300}$, 80% PBS) 30 min prior to the injection of C-2d. Additionally, healthy mice were also injected with 500 µCi C-2d. After 2 h of circulation time after the C-2d injection, the mice were sacrificed. Liver, tumor, muscle, and brain tissues were excised and embedded in O.C.T. compound (Sakura Finetek, Torrance, Calif.) and frozen at −20° C., and a series of 8 µm frozen sections was cut and mounted on microscope slides. To determine radiotracer distribution, digital autoradiography was performed by placing tissue sections in a film cassette against a phosphor image plate (BASMS-2325; Fujifilm) for 48 h at −20° C. Phosphor imaging plates were read at a pixel resolution of 25 µm with a Typhoon 7000IP plate reader (GE Healthcare, Piscataway, N.J.) (images not shown). After autoradiographic exposure, the same frozen sections were then used for immunohistochemical staining. Areas of brain slides containing tumor tissue were identified using the H&E staining and then overlaid with the autoradiographic data (images not shown). Intensity of tumor areas and non-tumor areas were then quantified using ImageJ 1.47 u (see FIGS. 5A and 5B).

Example 4.2.2. Autoradiography Using C-2f ($^{18}$F)

One day after PET/CT imaging, the same orthotopic U251 MG tumor bearing mice of Example 4.1.3 were administered with C-2f (80 µCi, 45 mCi/µmol in 300 µL 10% EtOH in 0.9% sterile saline) via tail vein injection. Blocked mice from the previous day received another dose of olaparib (500 mM, 3.7 µmol, in 100 µL 15% PEG$_{300}$/85% 0.9% saline). The mice were sacrificed after 2 hours and brain and muscle tissues harvested. The collected organs were fixed in Tissue-Tek O.C.T. compound (Sakura Finetek, Torrance, Calif.) and flash-frozen in liquid nitrogen and cut into 20 µm sections using a Vibratome Ultra Pro 5000 Cryostat (Vibratome, St. Louis, Mo.). A storage phosphor autoradiography plate (Fujifilm, BAS-MS2325, Fuji Photo Film, Japan) was exposed to the tissue slices overnight at −20° C. and read the following day (images not shown). Relative count intensity of the sections in each image was quantified using ImageJ 1.47 u processing software (see FIGS. 6A and 6B). Tumor/muscle and brain/muscle ratios were calculated using Prism 6.0c (GraphPad Software, La Jolla, Calif.). The same sections were subsequently subjected to H&E staining (hematoxylin-eosin) for morphological evaluation of tissue pathology and to compare the localization of the radiotracer with the location of tumor tissue (images not shown).

What is claimed is:

1. A chemical entity, which is a compound of formula (I):

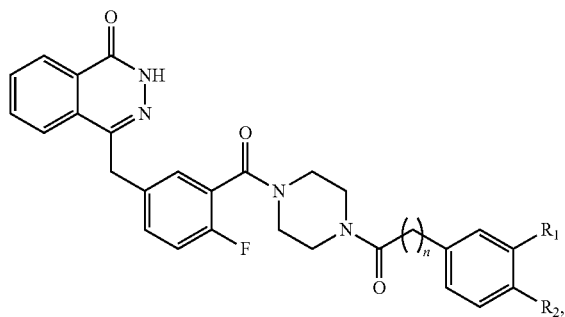

I or a pharmaceutically acceptable salt thereof, wherein:
one of $R_1$ and $R_2$ is $^{123}$I, $^{124}$I, $^{125}$I, $^{131}$I, $^{211}$At or $^{18}$F, and the other is H, $^{123}$I, $^{124}$I, $^{125}$I, $^{131}$I, $^{211}$At or $^{18}$F; and n is 0, 1 or 2.

2. The chemical entity of claim 1, wherein:
one of $R_1$ and $R_2$ is $^{123}$I, $^{124}$I, $^{125}$I, $^{131}$I, or $^{211}$At, and the other is H, $^{123}$I, $^{124}$I, $^{125}$I, $^{131}$I, or $^{211}$At.
3. The chemical entity of claim 1, wherein n is 0.
4. The chemical entity of claim 1, wherein n is 1.
5. The chemical entity of claim 1, wherein n is 2.
6. The chemical entity of claim 2, wherein n is 0.
7. The chemical entity of claim 2, wherein n is 1.
8. The chemical entity of claim 2, wherein n is 2.
9. The chemical entity of any of claims 1-8, wherein:
one of $R_1$ and $R_2$ is $^{123}$I or $^{125}$I, and the other is H.
10. The chemical entity of any of claims 1-8, wherein:
one of $R_1$ and $R_2$ is $^{123}$I, and the other is H.
11. The chemical entity of any of claims 1-8, wherein:
one of $R_1$ and $R_2$ is $^{131}$I, and the other is H.
12. The chemical entity of any of claims 1-8, wherein:
one of $R_1$ and $R_2$ is $^{211}$At, and the other is H.
13. The chemical entity of any of claims 1-8, wherein:
one of $R_1$ and $R_2$ is $^{124}$I, and the other is H.
14. The chemical entity of any of claim 1 or 3-5, wherein:
one of $R_1$ and $R_2$ is $^{18}$F, and the other is H.
15. The chemical entity of claim 1, which is the compound

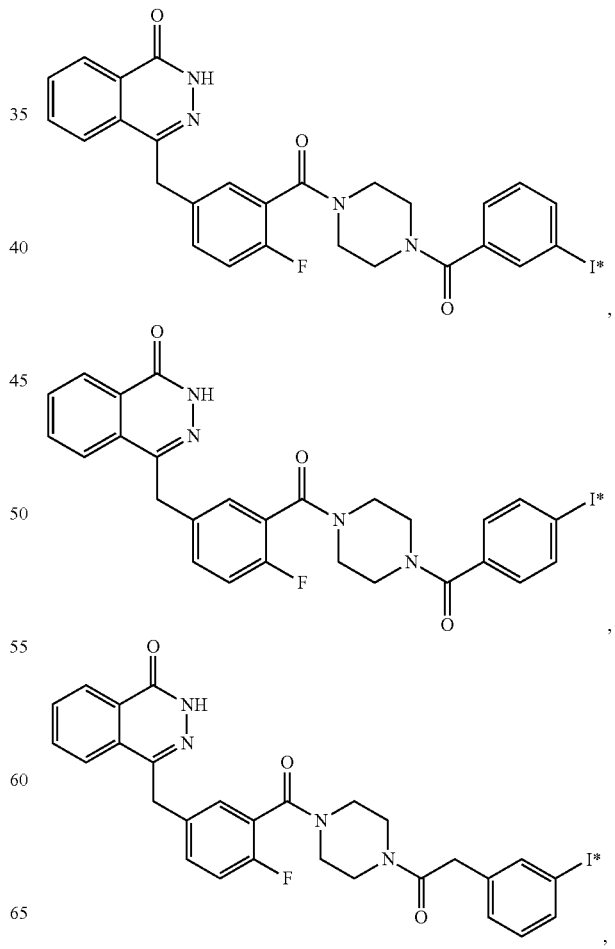

-continued

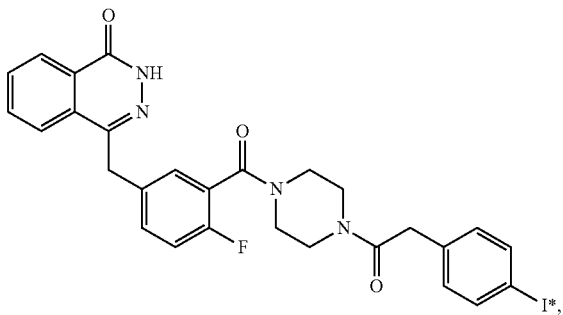

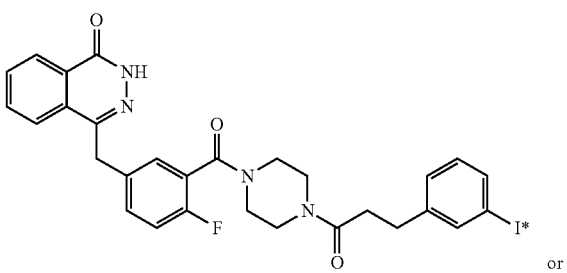

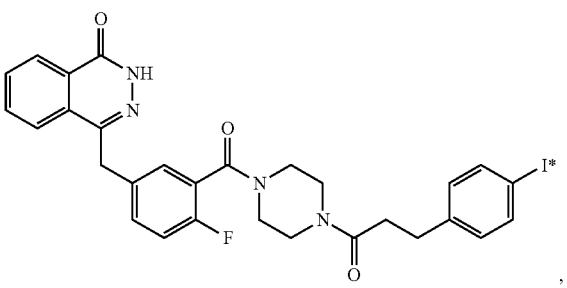

or a pharmaceutically acceptable salt thereof, wherein I* is $^{123}$I.

16. The chemical entity of claim 1, which is the compound

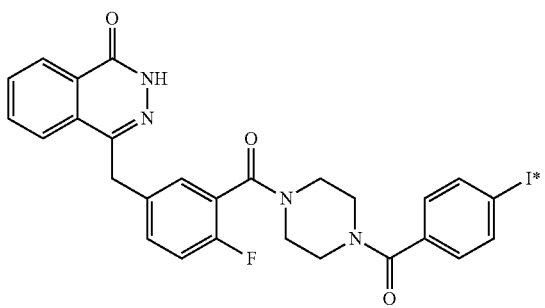

or a pharmaceutically acceptable salt thereof, wherein I* is $^{131}$I.

17. The chemical entity of claim 1, which is the compound

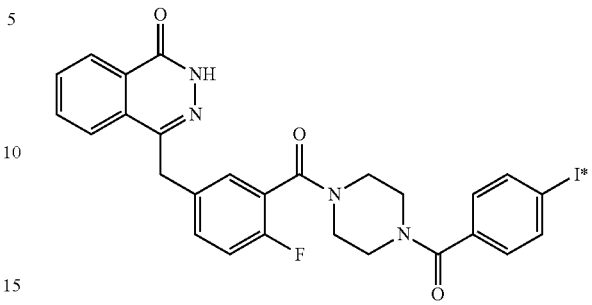

or a pharmaceutically acceptable salt thereof, wherein I* is $^{124}$I.

18. The chemical entity of claim 1, which is the compound

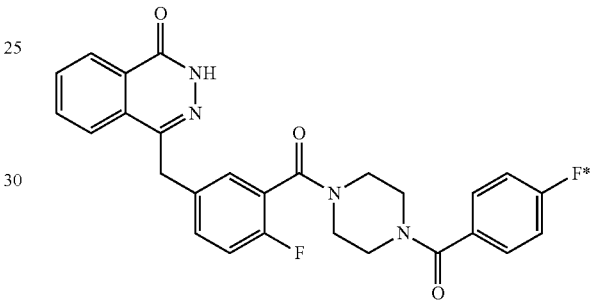

or a pharmaceutically acceptable salt thereof, wherein F* is $^{18}$F.

19. A composition comprising the chemical entity of any of claim 1-8 or 15-18 and a pharmaceutically acceptable carrier, adjuvant or vehicle.

20. A method of treating a disease or disorder characterized by overexpression of PARP1 in a patient in need of such treatment comprising administering an effective amount of the chemical entity of any of claim 1-8 or 15-18.

21. The method of claim 20, wherein the disease or disorder is cancer.

22. The method of claim 21, wherein the cancer comprises a brain malignancy.

23. The method of claim 21, wherein the cancer comprises glioma.

24. The method of claim 21, wherein the cancer comprises glioblastoma multiforme.

25. The method of claim 20, wherein said administering comprises parenteral administration.

26. The method of claim 20, wherein the patient has received or is receiving therapy that induces PARP1 expression or localization of PARP1 to DNA.

27. The method of claim 26, wherein said therapy comprises radiotherapy.

28. The method of claim 26, wherein said therapy comprises administration of a DNA-damaging agent.

29. A method for imaging a tumor in a subject, comprising:
    administering to the subject an image-generating amount of the chemical entity of any of claim 1-8 or 15-18; and measuring the distribution of the compound.

30. The method of claim 29, wherein the chemical entity is the chemical entity of claim 15 or claim 16.

31. The method of claim 30, wherein said measuring comprises single-photon emission computed tomography (SPECT).

32. The method of claim 29, wherein the chemical entity is the chemical entity of claim 17 or claim 18.

33. The method of claim 32, wherein said measuring comprises positron emission tomography (PET).

34. The method of claim 21, wherein said administering comprises parenteral administration.

35. The method of claim 22, wherein said administering comprises parenteral administration.

36. The method of claim 23, wherein said administering comprises parenteral administration.

37. The method of claim 24, wherein said administering comprises parenteral administration.

38. The method of claim 21, wherein the patient has received or is receiving therapy that induces PARP1 expression or localization of PARP1 to DNA.

39. The method of claim 22, wherein the patient has received or is receiving therapy that induces PARP1 expression or localization of PARP1 to DNA.

40. The method of claim 23, wherein the patient has received or is receiving therapy that induces PARP1 expression or localization of PARP1 to DNA.

41. The method of claim 24, wherein the patient has received or is receiving therapy that induces PARP1 expression or localization of PARP1 to DNA.

42. The method of claim 25, wherein the patient has received or is receiving therapy that induces PARP1 expression or localization of PARP1 to DNA.

43. The method of claim 34, wherein the patient has received or is receiving therapy that induces PARP1 expression or localization of PARP1 to DNA.

44. The method of claim 35, wherein the patient has received or is receiving therapy that induces PARP1 expression or localization of PARP1 to DNA.

45. The method of claim 36, wherein the patient has received or is receiving therapy that induces PARP1 expression or localization of PARP1 to DNA.

46. The method of claim 37, wherein the patient has received or is receiving therapy that induces PARP1 expression or localization of PARP1 to DNA.

47. A composition comprising the chemical entity of claim 9 and a pharmaceutically acceptable carrier, adjuvant or vehicle.

48. A composition comprising the chemical entity of claim 10 and a pharmaceutically acceptable carrier, adjuvant or vehicle.

49. A composition comprising the chemical entity of claim 11 and a pharmaceutically acceptable carrier, adjuvant or vehicle.

50. A composition comprising the chemical entity of claim 12 and a pharmaceutically acceptable carrier, adjuvant or vehicle.

51. A composition comprising the chemical entity of claim 13 and a pharmaceutically acceptable carrier, adjuvant or vehicle.

52. A composition comprising the chemical entity of claim 14 and a pharmaceutically acceptable carrier, adjuvant or vehicle.

* * * * *

UNITED STATES PATENT AND TRADEMARK OFFICE
CERTIFICATE OF CORRECTION

| | |
|---|---|
| PATENT NO. | : 10,512,700 B2 |
| APPLICATION NO. | : 15/506001 |
| DATED | : December 24, 2019 |
| INVENTOR(S) | : Thomas Reiner et al. |

It is certified that error appears in the above-identified patent and that said Letters Patent is hereby corrected as shown below:

In the Specification

In Column 1, please add the following text after Line 9, before the heading "BACKGROUND":
--GOVERNMENT SUPPORT
This invention was made with government support under CA191679 awarded by the National Institutes of Health. The government has certain rights in the invention.--

Signed and Sealed this
Nineteenth Day of March, 2024

Katherine Kelly Vidal
*Director of the United States Patent and Trademark Office*